(12) United States Patent
Mason et al.

(10) Patent No.: US 12,301,663 B2
(45) Date of Patent: *May 13, 2025

(54) SYSTEM AND METHOD FOR TRANSMITTING DATA AND ORDERING ASYNCHRONOUS DATA

(71) Applicant: ROM TECHNOLOGIES, INC., Brookfield, CT (US)

(72) Inventors: Steven Mason, Las Vegas, NV (US); Daniel Posnack, Fort Lauderdale, FL (US); Peter Arn, Roxbury, CT (US); Wendy Para, Las Vegas, NV (US); S. Adam Hacking, Nashua, NH (US); Micheal Mueller, Oil City, PA (US); Joseph Guaneri, Merrick, NY (US); Jonathan Greene, Denver, CO (US)

(73) Assignee: ROM Technologies, Inc., Brookfield, CT (US)

( * ) Notice: Subject to any disclaimer, the term of this patent is extended or adjusted under 35 U.S.C. 154(b) by 324 days.

This patent is subject to a terminal disclaimer.

(21) Appl. No.: 17/589,409

(22) Filed: Jan. 31, 2022

(65) Prior Publication Data

US 2022/0158916 A1    May 19, 2022

Related U.S. Application Data

(63) Continuation of application No. 17/149,457, filed on Jan. 14, 2021, now Pat. No. 11,265,234, which is a
(Continued)

(51) Int. Cl.
*G16H 10/60*    (2018.01)
*G16H 20/00*    (2018.01)
(Continued)

(52) U.S. Cl.
CPC .............. *H04L 67/12* (2013.01); *H04L 43/06* (2013.01); *H04L 47/43* (2022.05); *H04L 49/552* (2013.01);
(Continued)

(58) Field of Classification Search
CPC ...... A61B 5/0002–02; A61B 34/10–25; A61B 2505/01–09;
(Continued)

(56) References Cited

U.S. PATENT DOCUMENTS

| 823,712 A | 6/1906 | Uhlmann |
| 4,499,900 A | 2/1985 | Petrofsky et al. |

(Continued)

FOREIGN PATENT DOCUMENTS

| CA | 3193419 A1 | 3/2022 |
| CN | 2885238 Y | 4/2007 |

(Continued)

OTHER PUBLICATIONS

Alcaraz et al., "Machine Learning as Digital Therapy Assessment for Mobile Gait Rehabilitation," 2018 IEEE 28th International Workshop on Machine Learning for Signal Processing (MLSP), Aalborg, Denmark, 2018, 6 pages.
(Continued)

*Primary Examiner* — Timothy J Weidner
(74) *Attorney, Agent, or Firm* — Dickinson Wright PLLC; Jonathan H. Harder; Stephen A. Mason

(57) ABSTRACT

A computer-implemented system includes an electromechanical device configured to be manipulated by a patient while performing an exercise session, and a processor in communication with the electromechanical device. The processor is configured to receive data, generate a map packet, and transmit the map packet. The processor is configured to use the data to generate continuity packets, where each of
(Continued)

the continuity packets includes a contiguous portion of the data, and transmit the continuity packets. The processor is configured to use the map packet and the continuity packets to cause an output file to be generated.

18 Claims, 7 Drawing Sheets

Related U.S. Application Data continuation-in-part of application No. 17/021,895, filed on Sep. 15, 2020, now Pat. No. 11,071,597.

(60) Provisional application No. 63/028,399, filed on May 21, 2020, provisional application No. 62/910,232, filed on Oct. 3, 2019.

(51) Int. Cl.
| | |
|---|---|
| *G16H 40/67* | (2018.01) |
| *G16H 80/00* | (2018.01) |
| *G16Y 10/60* | (2020.01) |
| *G16Y 20/40* | (2020.01) |
| *G16Y 40/10* | (2020.01) |
| *G16Y 40/20* | (2020.01) |
| *H04L 43/06* | (2022.01) |
| *H04L 47/43* | (2022.01) |
| *H04L 49/552* | (2022.01) |
| *H04L 67/12* | (2022.01) |
| *H04L 69/22* | (2022.01) |

(52) U.S. Cl.
CPC .......... *H04L 69/22* (2013.01); *A61B 2505/09* (2013.01); *A63B 2225/20* (2013.01); *G16H 10/60* (2018.01); *G16H 20/00* (2018.01); *G16H 40/67* (2018.01); *G16H 80/00* (2018.01); *G16Y 10/60* (2020.01); *G16Y 20/40* (2020.01); *G16Y 40/10* (2020.01); *G16Y 40/20* (2020.01); *H04L 2212/00* (2013.01)

(58) Field of Classification Search
CPC ....... A61B 2034/101–258; A63B 22/06–0694; A63B 24/0062–0087; A63B 2024/0065–0096; A63B 2225/20; G16H 10/20–65; G16H 15/00; G16H 20/00–90; G16H 40/20–67; G16H 80/00; G16Y 10/60–65; G16Y 20/40; G16Y 40/10–20; H04L 43/02–55; H04L 47/43–431; H04L 49/55–557; H04L 49/9057–9078; H04L 67/12–125; H04L 69/22–28; H04L 2212/00

See application file for complete search history.

(56) References Cited

U.S. PATENT DOCUMENTS

| | | |
|---|---|---|
| 4,822,032 A | 4/1989 | Whitmore et al. |
| 4,860,763 A | 8/1989 | Schminke |
| 4,869,497 A | 9/1989 | Stewart et al. |
| 4,932,650 A | 6/1990 | Bingham et al. |
| 5,137,501 A | 8/1992 | Mertesdorf |
| 5,161,430 A | 11/1992 | Febey |
| 5,202,794 A | 4/1993 | Schnee et al. |
| 5,240,417 A | 8/1993 | Smithson et al. |
| 5,247,853 A | 9/1993 | Dalebout |
| 5,256,117 A | 10/1993 | Potts et al. |
| D342,299 S | 12/1993 | Birrell et al. |
| 5,282,748 A | 2/1994 | Little |
| 5,284,131 A | 2/1994 | Gray |
| 5,316,532 A | 5/1994 | Butler |
| 5,318,487 A | 6/1994 | Golen |
| 5,324,241 A | 6/1994 | Artigues et al. |
| 5,336,147 A | 8/1994 | Sweeney, III |
| 5,338,272 A | 8/1994 | Sweeney, III |
| 5,356,356 A | 10/1994 | Hildebrandt |
| 5,361,649 A | 11/1994 | Slocum, Jr. |
| D359,777 S | 6/1995 | Hildebrandt |
| 5,429,140 A | 7/1995 | Burdea et al. |
| 5,458,022 A | 10/1995 | Mattfeld et al. |
| 5,487,713 A | 1/1996 | Butler |
| 5,566,589 A | 10/1996 | Buck |
| 5,580,338 A | 12/1996 | Scelta et al. |
| 5,676,349 A | 10/1997 | Wilson |
| 5,685,804 A | 11/1997 | Whan-Tong et al. |
| 5,738,636 A | 4/1998 | Saringer et al. |
| 5,860,941 A | 1/1999 | Saringer et al. |
| 5,950,813 A | 9/1999 | Hoskins et al. |
| 6,007,459 A | 12/1999 | Burgess |
| D421,075 S | 2/2000 | Hildebrandt |
| 6,053,847 A | 4/2000 | Stearns et al. |
| 6,077,201 A | 6/2000 | Cheng |
| 6,102,834 A | 8/2000 | Chen |
| 6,110,130 A | 8/2000 | Kramer |
| 6,155,958 A | 12/2000 | Goldberg |
| 6,162,189 A | 12/2000 | Girone et al. |
| 6,182,029 B1 | 1/2001 | Friedman |
| D438,580 S | 3/2001 | Shaw |
| 6,253,638 B1 | 7/2001 | Bermudez |
| 6,267,735 B1 | 7/2001 | Blanchard et al. |
| 6,273,863 B1 | 8/2001 | Avni et al. |
| D450,100 S | 11/2001 | Hsu |
| D450,101 S | 11/2001 | Hsu |
| D451,972 S | 12/2001 | Easley |
| D452,285 S | 12/2001 | Easley |
| D454,605 S | 3/2002 | Lee |
| 6,371,891 B1 | 4/2002 | Speas |
| D459,776 S | 7/2002 | Lee |
| 6,413,190 B1 | 7/2002 | Wood et al. |
| 6,430,436 B1 | 8/2002 | Richter |
| 6,436,058 B1 | 8/2002 | Krahner et al. |
| 6,450,923 B1 | 9/2002 | Vatti |
| 6,474,193 B1 | 11/2002 | Farney |
| 6,491,649 B1 | 12/2002 | Ombrellaro |
| 6,514,085 B2 | 2/2003 | Slattery et al. |
| 6,535,861 B1 | 3/2003 | OConnor et al. |
| 6,543,309 B2 | 4/2003 | Heim |
| 6,589,139 B1 | 7/2003 | Butterworth |
| 6,601,016 B1 | 7/2003 | Brown et al. |
| 6,602,191 B2 | 8/2003 | Quy |
| 6,613,000 B1 | 9/2003 | Reinkensmeyer et al. |
| 6,626,800 B1 | 9/2003 | Casler |
| 6,626,805 B1 | 9/2003 | Lightbody |
| 6,640,122 B2 | 10/2003 | Manoli |
| 6,640,662 B1 | 11/2003 | Baxter |
| 6,652,425 B1 | 11/2003 | Martin et al. |
| 6,820,517 B1 | 11/2004 | Farney |
| 6,865,969 B2 | 3/2005 | Stevens |
| 6,890,312 B1 | 5/2005 | Priester et al. |
| 6,895,834 B1 | 5/2005 | Baatz |
| 6,902,513 B1 | 6/2005 | McClure |
| 7,058,453 B2 | 6/2006 | Nelson et al. |
| 7,063,643 B2 | 6/2006 | Arai |
| 7,156,665 B1 | 1/2007 | OConnor et al. |
| 7,156,780 B1 | 1/2007 | Fuchs et al. |
| 7,169,085 B1 | 1/2007 | Killin et al. |
| 7,204,788 B2 | 4/2007 | Andrews |
| 7,209,886 B2 | 4/2007 | Kimmel |
| 7,226,394 B2 | 6/2007 | Johnson |
| RE39,904 E | 10/2007 | Lee |
| 7,406,003 B2 | 7/2008 | Burkhardt et al. |
| 7,507,188 B2 | 3/2009 | Nurre |
| 7,594,879 B2 | 9/2009 | Johnson |
| 7,628,730 B1 | 12/2009 | Watterson et al. |
| D610,635 S | 2/2010 | Hildebrandt |
| 7,778,851 B2 | 8/2010 | Schoenberg et al. |
| 7,809,601 B2 | 10/2010 | Shaya et al. |
| 7,815,551 B2 | 10/2010 | Merli |
| 7,833,135 B2 | 11/2010 | Radow et al. |
| 7,837,472 B1 | 11/2010 | Elsmore et al. |

(56) References Cited

U.S. PATENT DOCUMENTS

| | | |
|---|---|---|
| 7,955,219 B2 | 6/2011 | Birrell et al. |
| 7,969,315 B1 | 6/2011 | Ross et al. |
| 7,988,599 B2 | 8/2011 | Ainsworth et al. |
| 8,012,107 B2 | 9/2011 | Einav et al. |
| 8,021,270 B2 | 9/2011 | D'Eredita |
| 8,038,578 B2 | 10/2011 | Olrik et al. |
| 8,079,937 B2 | 12/2011 | Bedell et al. |
| 8,113,991 B2 | 2/2012 | Kutliroff |
| 8,172,724 B2 | 5/2012 | Solomon |
| 8,177,732 B2 | 5/2012 | Einav et al. |
| 8,287,434 B2 | 10/2012 | Zavadsky et al. |
| 8,298,123 B2 | 10/2012 | Hickman |
| 8,371,990 B2 | 2/2013 | Shea |
| 8,419,593 B2 | 4/2013 | Ainsworth et al. |
| 8,465,398 B2 | 6/2013 | Lee et al. |
| 8,506,458 B2 | 8/2013 | Dugan |
| 8,515,777 B1 | 8/2013 | Rajasenan |
| 8,540,515 B2 | 9/2013 | Williams et al. |
| 8,540,516 B2 | 9/2013 | Williams et al. |
| 8,556,778 B1 | 10/2013 | Dugan |
| 8,607,465 B1 | 12/2013 | Edwards |
| 8,613,689 B2 | 12/2013 | Dyer et al. |
| 8,615,529 B2 | 12/2013 | Reiner |
| 8,672,812 B2 | 3/2014 | Dugan |
| 8,751,264 B2 | 6/2014 | Beraja et al. |
| 8,784,273 B2 | 7/2014 | Dugan |
| 8,818,496 B2 | 8/2014 | Dziubinski et al. |
| 8,823,448 B1 | 9/2014 | Shen |
| 8,845,493 B2 | 9/2014 | Watterson et al. |
| 8,849,681 B2 | 9/2014 | Hargrove et al. |
| 8,864,628 B2 | 10/2014 | Boyette et al. |
| 8,893,287 B2 | 11/2014 | Gjonej et al. |
| 8,911,327 B1 | 12/2014 | Boyette |
| 8,979,711 B2 | 3/2015 | Dugan |
| 9,004,598 B2 | 4/2015 | Weber |
| 9,044,630 B1 | 6/2015 | Lampert et al. |
| 9,167,281 B2 | 10/2015 | Petrov et al. |
| D744,050 S | 11/2015 | Colburn |
| 9,248,071 B1 | 2/2016 | Benda et al. |
| 9,272,185 B2 | 3/2016 | Dugan |
| 9,283,434 B1 | 3/2016 | Wu |
| 9,295,878 B2 | 3/2016 | Corbalis et al. |
| 9,311,789 B1 | 4/2016 | Gwin |
| 9,312,907 B2 | 4/2016 | Auchinleck et al. |
| 9,367,668 B2 | 6/2016 | Flynt et al. |
| 9,409,054 B2 | 8/2016 | Dugan |
| 9,443,205 B2 | 9/2016 | Wall |
| 9,474,935 B2 | 10/2016 | Abbondanza et al. |
| 9,480,873 B2 | 11/2016 | Chuang |
| 9,481,428 B2 | 11/2016 | Gros et al. |
| 9,514,277 B2 | 12/2016 | Hassing et al. |
| 9,566,472 B2 | 2/2017 | Dugan |
| 9,579,056 B2 | 2/2017 | Rosenbek et al. |
| 9,629,558 B2 | 4/2017 | Yuen et al. |
| 9,640,057 B1 | 5/2017 | Ross |
| 9,707,147 B2 | 7/2017 | Levital et al. |
| 9,713,744 B2 | 7/2017 | Suzuki |
| D794,142 S | 8/2017 | Zhou |
| 9,717,947 B2 | 8/2017 | Lin |
| 9,737,761 B1 | 8/2017 | Govindarajan |
| 9,757,612 B2 | 9/2017 | Weber |
| 9,782,621 B2 | 10/2017 | Chiang et al. |
| 9,802,076 B2 | 10/2017 | Murray et al. |
| 9,802,081 B2 | 10/2017 | Ridgel et al. |
| 9,813,239 B2 | 11/2017 | Chee et al. |
| 9,827,445 B2 | 11/2017 | Marcos et al. |
| 9,849,337 B2 | 12/2017 | Roman et al. |
| 9,868,028 B2 | 1/2018 | Shin |
| 9,872,087 B2 | 1/2018 | DelloStritto et al. |
| 9,872,637 B2 | 1/2018 | Kording et al. |
| 9,914,053 B2 | 3/2018 | Dugan |
| 9,919,198 B2 | 3/2018 | Romeo et al. |
| 9,937,382 B2 | 4/2018 | Dugan |
| 9,939,784 B1 | 4/2018 | Berardinelli |
| 9,977,587 B2 | 5/2018 | Mountain |
| 9,993,181 B2 | 6/2018 | Ross |
| 9,997,082 B2 | 6/2018 | Kaleal |
| 10,004,946 B2 | 6/2018 | Ross |
| 10,026,052 B2 | 7/2018 | Brown et al. |
| D826,349 S | 8/2018 | Oblamski |
| 10,055,550 B2 | 8/2018 | Goetz |
| 10,058,473 B2 | 8/2018 | Oshima et al. |
| 10,074,148 B2 | 9/2018 | Cashman et al. |
| 10,089,443 B2 | 10/2018 | Miller et al. |
| 10,111,643 B2 | 10/2018 | Shulhauser et al. |
| 10,130,311 B1 | 11/2018 | De Sapio et al. |
| 10,137,328 B2 | 11/2018 | Baudhuin |
| 10,143,395 B2 | 12/2018 | Chakravarthy et al. |
| 10,155,134 B2 | 12/2018 | Dugan |
| 10,159,872 B2 | 12/2018 | Sasaki et al. |
| 10,173,094 B2 | 1/2019 | Gomberg et al. |
| 10,173,095 B2 | 1/2019 | Gomberg et al. |
| 10,173,096 B2 | 1/2019 | Gomberg et al. |
| 10,173,097 B2 | 1/2019 | Gomberg et al. |
| 10,198,928 B1 | 2/2019 | Ross et al. |
| 10,226,663 B2 | 3/2019 | Gomberg et al. |
| 10,231,664 B2 | 3/2019 | Ganesh |
| 10,244,990 B2 | 4/2019 | Hu et al. |
| 10,258,823 B2 | 4/2019 | Cole |
| 10,322,315 B2 | 6/2019 | Foley et al. |
| 10,325,070 B2 | 6/2019 | Beale et al. |
| 10,327,697 B1 | 6/2019 | Stein et al. |
| 10,369,021 B2 | 8/2019 | Zoss et al. |
| 10,380,866 B1 | 8/2019 | Ross et al. |
| 10,413,222 B2 | 9/2019 | Kayyali |
| 10,413,238 B1 | 9/2019 | Cooper |
| 10,424,033 B2 | 9/2019 | Romeo |
| 10,430,552 B2 | 10/2019 | Mihai |
| D866,957 S | 11/2019 | Ross et al. |
| 10,468,131 B2 | 11/2019 | Macoviak et al. |
| 10,475,323 B1 | 11/2019 | Ross |
| 10,475,537 B2 | 11/2019 | Purdie et al. |
| 10,492,977 B2 | 12/2019 | Kapure et al. |
| 10,507,358 B2 | 12/2019 | Kinnunen et al. |
| 10,542,914 B2 | 1/2020 | Forth et al. |
| 10,546,467 B1 | 1/2020 | Luciano, Jr. et al. |
| 10,569,122 B2 | 2/2020 | Johnson |
| 10,572,626 B2 | 2/2020 | Balram |
| 10,576,331 B2 | 3/2020 | Kuo |
| 10,581,896 B2 | 3/2020 | Nachenberg |
| 10,625,114 B2 | 4/2020 | Ercanbrack |
| 10,646,746 B1 | 5/2020 | Gomberg et al. |
| 10,660,534 B2 | 5/2020 | Lee et al. |
| 10,678,890 B2 | 6/2020 | Bitran et al. |
| 10,685,092 B2 | 6/2020 | Paparella et al. |
| 10,777,200 B2 | 9/2020 | Will et al. |
| D899,605 S | 10/2020 | Ross et al. |
| 10,792,495 B2 | 10/2020 | Izvorski et al. |
| 10,814,170 B2 | 10/2020 | Wang et al. |
| 10,857,426 B1 | 12/2020 | Neumann |
| 10,867,695 B2 | 12/2020 | Neagle |
| 10,874,905 B2 | 12/2020 | Belson et al. |
| D907,143 S | 1/2021 | Ach et al. |
| 10,881,911 B2 | 1/2021 | Kwon et al. |
| 10,918,332 B2 | 2/2021 | Belson et al. |
| 10,931,643 B1 | 2/2021 | Neumann |
| 10,987,176 B2 | 4/2021 | Poltaretskyi et al. |
| 10,991,463 B2 | 4/2021 | Kutzko et al. |
| 11,000,735 B2 | 5/2021 | Orady et al. |
| 11,045,709 B2 | 6/2021 | Putnam |
| 11,065,170 B2 | 7/2021 | Yang et al. |
| 11,065,527 B2 | 7/2021 | Putnam |
| 11,069,436 B2 | 7/2021 | Mason et al. |
| 11,071,597 B2 | 7/2021 | Posnack et al. |
| 11,075,000 B2 | 7/2021 | Mason et al. |
| D928,635 S | 8/2021 | Hacking et al. |
| 11,087,865 B2 | 8/2021 | Mason et al. |
| 11,094,400 B2 | 8/2021 | Riley et al. |
| 11,101,028 B2 | 8/2021 | Mason et al. |
| 11,107,591 B1 | 8/2021 | Mason |
| 11,139,060 B2 | 10/2021 | Mason et al. |
| 11,185,735 B2 | 11/2021 | Am et al. |
| 11,185,738 B1 | 11/2021 | McKirdy et al. |
| D939,096 S | 12/2021 | Lee |

(56) References Cited

U.S. PATENT DOCUMENTS

| | | |
|---|---|---|
| D939,644 S | 12/2021 | Ach et al. |
| D940,797 S | 1/2022 | Ach et al. |
| D940,891 S | 1/2022 | Lee |
| 11,229,727 B2 | 1/2022 | Tatonetti |
| 11,265,234 B2 * | 3/2022 | Guaneri .................. H04L 67/12 |
| 11,270,795 B2 | 3/2022 | Mason et al. |
| 11,272,879 B2 | 3/2022 | Wiedenhoefer et al. |
| 11,278,766 B2 | 3/2022 | Lee |
| 11,282,599 B2 | 3/2022 | Mason et al. |
| 11,282,604 B2 | 3/2022 | Mason et al. |
| 11,282,608 B2 | 3/2022 | Mason et al. |
| 11,284,797 B2 | 3/2022 | Mason et al. |
| D948,639 S | 4/2022 | Ach et al. |
| 11,295,848 B2 | 4/2022 | Mason et al. |
| 11,298,284 B2 | 4/2022 | Bayerlein |
| 11,309,085 B2 | 4/2022 | Mason et al. |
| 11,317,975 B2 | 5/2022 | Mason et al. |
| 11,325,005 B2 | 5/2022 | Mason et al. |
| 11,328,807 B2 | 5/2022 | Mason et al. |
| 11,337,648 B2 | 5/2022 | Mason |
| 11,347,829 B1 | 5/2022 | Sclar et al. |
| 11,348,683 B2 | 5/2022 | Guaneri et al. |
| 11,376,470 B2 | 7/2022 | Weldemariam |
| 11,404,150 B2 | 8/2022 | Guaneri et al. |
| 11,410,768 B2 | 8/2022 | Mason et al. |
| 11,422,841 B2 | 8/2022 | Jeong |
| 11,437,137 B1 | 9/2022 | Harris |
| 11,495,355 B2 | 11/2022 | McNutt et al. |
| 11,508,258 B2 | 11/2022 | Nakashima et al. |
| 11,508,482 B2 | 11/2022 | Mason et al. |
| 11,515,021 B2 | 11/2022 | Mason |
| 11,515,028 B2 | 11/2022 | Mason |
| 11,524,210 B2 | 12/2022 | Kim et al. |
| 11,527,326 B2 | 12/2022 | McNair et al. |
| 11,532,402 B2 | 12/2022 | Farley et al. |
| 11,534,654 B2 | 12/2022 | Silcock et al. |
| D976,339 S | 1/2023 | Li |
| 11,541,274 B2 | 1/2023 | Hacking |
| 11,553,969 B1 | 1/2023 | Lang et al. |
| 11,621,067 B1 | 4/2023 | Nolan |
| 11,636,944 B2 | 4/2023 | Hanrahan et al. |
| 11,654,327 B2 | 5/2023 | Phillips et al. |
| 11,663,673 B2 | 5/2023 | Pyles |
| 11,701,548 B2 | 7/2023 | Posnack et al. |
| 11,957,960 B2 | 4/2024 | Bissonnette et al. |
| 12,057,210 B2 | 8/2024 | Akinola et al. |
| 12,205,704 B2 | 1/2025 | Hosoi et al. |
| 2001/0044573 A1 | 11/2001 | Manoli |
| 2002/0010596 A1 | 1/2002 | Matory |
| 2002/0072452 A1 | 6/2002 | Torkelson |
| 2002/0143279 A1 | 10/2002 | Porter et al. |
| 2002/0160883 A1 | 10/2002 | Dugan |
| 2002/0183599 A1 | 12/2002 | Castellanos |
| 2003/0013072 A1 | 1/2003 | Thomas |
| 2003/0036683 A1 | 2/2003 | Kehr et al. |
| 2003/0064860 A1 | 4/2003 | Yamashita et al. |
| 2003/0064863 A1 | 4/2003 | Chen |
| 2003/0083596 A1 | 5/2003 | Kramer et al. |
| 2003/0092536 A1 | 5/2003 | Romanelli et al. |
| 2003/0181832 A1 | 9/2003 | Carnahan et al. |
| 2004/0072652 A1 | 4/2004 | Alessandri et al. |
| 2004/0102931 A1 | 5/2004 | Ellis et al. |
| 2004/0106502 A1 | 6/2004 | Sher |
| 2004/0147969 A1 | 7/2004 | Mann et al. |
| 2004/0172093 A1 | 9/2004 | Rummerfield |
| 2004/0194572 A1 | 10/2004 | Kim |
| 2004/0197727 A1 | 10/2004 | Sachdeva et al. |
| 2004/0204959 A1 | 10/2004 | Moreano et al. |
| 2005/0015118 A1 | 1/2005 | Davis et al. |
| 2005/0020411 A1 | 1/2005 | Andrews |
| 2005/0043153 A1 | 2/2005 | Krietzman |
| 2005/0049122 A1 | 3/2005 | Vallone et al. |
| 2005/0085346 A1 | 4/2005 | Johnson |
| 2005/0085353 A1 | 4/2005 | Johnson |
| 2005/0115561 A1 | 6/2005 | Stahmann |
| 2005/0143641 A1 * | 6/2005 | Tashiro .................. G16H 30/20 |
| 2005/0274220 A1 | 12/2005 | Reboullet |
| 2006/0003871 A1 | 1/2006 | Houghton et al. |
| 2006/0046905 A1 | 3/2006 | Doody et al. |
| 2006/0058648 A1 | 3/2006 | Meier |
| 2006/0064136 A1 | 3/2006 | Wang |
| 2006/0064329 A1 | 3/2006 | Abolfathi et al. |
| 2006/0129432 A1 | 6/2006 | Choi et al. |
| 2006/0199700 A1 | 9/2006 | LaStayo et al. |
| 2006/0247095 A1 | 11/2006 | Rummerfield |
| 2007/0042868 A1 | 2/2007 | Fisher et al. |
| 2007/0118389 A1 | 5/2007 | Shipon |
| 2007/0137307 A1 | 6/2007 | Gruben et al. |
| 2007/0173392 A1 | 7/2007 | Stanford |
| 2007/0184414 A1 | 8/2007 | Perez |
| 2007/0194939 A1 | 8/2007 | Alvarez et al. |
| 2007/0219059 A1 | 9/2007 | Schwartz |
| 2007/0271065 A1 | 11/2007 | Gupta et al. |
| 2007/0287597 A1 | 12/2007 | Cameron |
| 2008/0021834 A1 | 1/2008 | Holla et al. |
| 2008/0077619 A1 | 3/2008 | Gilley et al. |
| 2008/0082356 A1 | 4/2008 | Friedlander et al. |
| 2008/0096726 A1 | 4/2008 | Riley et al. |
| 2008/0153592 A1 | 6/2008 | James-Herbert |
| 2008/0161166 A1 | 7/2008 | Lo |
| 2008/0161733 A1 | 7/2008 | Einav et al. |
| 2008/0183500 A1 | 7/2008 | Banigan |
| 2008/0281633 A1 | 11/2008 | Burdea et al. |
| 2008/0300914 A1 | 12/2008 | Karkanias et al. |
| 2009/0011907 A1 | 1/2009 | Radow et al. |
| 2009/0058635 A1 | 3/2009 | LaLonde et al. |
| 2009/0070138 A1 | 3/2009 | Langheier et al. |
| 2009/0211395 A1 | 8/2009 | Mule |
| 2009/0270227 A1 | 10/2009 | Ashby et al. |
| 2009/0287503 A1 | 11/2009 | Angell et al. |
| 2009/0299766 A1 | 12/2009 | Friedlander et al. |
| 2010/0048358 A1 | 2/2010 | Tchao et al. |
| 2010/0076786 A1 | 3/2010 | Dalton et al. |
| 2010/0121160 A1 | 5/2010 | Stark et al. |
| 2010/0173747 A1 | 7/2010 | Chen et al. |
| 2010/0216168 A1 | 8/2010 | Heinzman et al. |
| 2010/0234184 A1 | 9/2010 | Le Page et al. |
| 2010/0248899 A1 | 9/2010 | Bedell et al. |
| 2010/0248905 A1 | 9/2010 | Lu |
| 2010/0262052 A1 | 10/2010 | Lunau et al. |
| 2010/0268304 A1 | 10/2010 | Matos |
| 2010/0298102 A1 | 11/2010 | Bosecker et al. |
| 2010/0326207 A1 | 12/2010 | Topel |
| 2011/0010188 A1 | 1/2011 | Yoshikawa et al. |
| 2011/0047108 A1 | 2/2011 | Chakrabarty et al. |
| 2011/0119212 A1 | 5/2011 | De Bruin et al. |
| 2011/0172059 A1 | 7/2011 | Watterson et al. |
| 2011/0195819 A1 | 8/2011 | Shaw et al. |
| 2011/0218814 A1 | 9/2011 | Coats |
| 2011/0275483 A1 | 11/2011 | Dugan |
| 2011/0281249 A1 | 11/2011 | Gammell et al. |
| 2011/0306846 A1 | 12/2011 | Osorio |
| 2012/0041771 A1 | 2/2012 | Cosentino et al. |
| 2012/0065987 A1 | 3/2012 | Farooq et al. |
| 2012/0116258 A1 | 5/2012 | Lee |
| 2012/0130196 A1 | 5/2012 | Jain et al. |
| 2012/0130197 A1 | 5/2012 | Kugler et al. |
| 2012/0167709 A1 | 7/2012 | Chen et al. |
| 2012/0183939 A1 | 7/2012 | Aragones et al. |
| 2012/0190502 A1 | 7/2012 | Paulus et al. |
| 2012/0232438 A1 | 9/2012 | Cataldi et al. |
| 2012/0259648 A1 | 10/2012 | Mallon et al. |
| 2012/0259649 A1 | 10/2012 | Mallon et al. |
| 2012/0278759 A1 | 11/2012 | Curl et al. |
| 2012/0295240 A1 | 11/2012 | Walker et al. |
| 2012/0296455 A1 | 11/2012 | Ohnemus et al. |
| 2012/0310667 A1 | 12/2012 | Altman et al. |
| 2013/0108594 A1 | 5/2013 | Martin-Rendon et al. |
| 2013/0110545 A1 | 5/2013 | Smallwood |
| 2013/0123071 A1 | 5/2013 | Rhea |
| 2013/0123667 A1 | 5/2013 | Komatireddy et al. |
| 2013/0137550 A1 | 5/2013 | Skinner et al. |
| 2013/0137552 A1 | 5/2013 | Kemp et al. |
| 2013/0178334 A1 | 7/2013 | Brammer |

(56) References Cited

U.S. PATENT DOCUMENTS

| | | |
|---|---|---|
| 2013/0211281 A1 | 8/2013 | Ross et al. |
| 2013/0253943 A1 | 9/2013 | Lee et al. |
| 2013/0274069 A1 | 10/2013 | Watterson et al. |
| 2013/0296987 A1 | 11/2013 | Rogers et al. |
| 2013/0318027 A1 | 11/2013 | Almogy et al. |
| 2013/0332616 A1 | 12/2013 | Landwehr |
| 2013/0345025 A1 | 12/2013 | van der Merwe |
| 2014/0006042 A1 | 1/2014 | Keefe et al. |
| 2014/0011640 A1 | 1/2014 | Dugan |
| 2014/0031174 A1 | 1/2014 | Huang |
| 2014/0062900 A1 | 3/2014 | Kaula et al. |
| 2014/0074179 A1 | 3/2014 | Heldman et al. |
| 2014/0089836 A1 | 3/2014 | Damani et al. |
| 2014/0113261 A1 | 4/2014 | Akiba |
| 2014/0113768 A1 | 4/2014 | Lin et al. |
| 2014/0155129 A1 | 6/2014 | Dugan |
| 2014/0163439 A1 | 6/2014 | Uryash et al. |
| 2014/0172442 A1 | 6/2014 | Broderick |
| 2014/0172460 A1 | 6/2014 | Kohli |
| 2014/0172514 A1 | 6/2014 | Schumann et al. |
| 2014/0188009 A1 | 7/2014 | Lange et al. |
| 2014/0194250 A1 | 7/2014 | Reich et al. |
| 2014/0194251 A1 | 7/2014 | Reich et al. |
| 2014/0207264 A1 | 7/2014 | Quy |
| 2014/0207486 A1 | 7/2014 | Carty et al. |
| 2014/0228649 A1 | 8/2014 | Rayner et al. |
| 2014/0246499 A1 | 9/2014 | Proud et al. |
| 2014/0256511 A1 | 9/2014 | Smith |
| 2014/0257837 A1 | 9/2014 | Walker et al. |
| 2014/0274565 A1 | 9/2014 | Boyette et al. |
| 2014/0274622 A1 | 9/2014 | Leonhard |
| 2014/0303540 A1 | 10/2014 | Baym |
| 2014/0309083 A1 | 10/2014 | Dugan |
| 2014/0322686 A1 | 10/2014 | Kang |
| 2014/0347265 A1 | 11/2014 | Aimone et al. |
| 2014/0371816 A1 | 12/2014 | Matos |
| 2014/0372133 A1 | 12/2014 | Austrum et al. |
| 2015/0025816 A1 | 1/2015 | Ross |
| 2015/0045700 A1 | 2/2015 | Cavanagh et al. |
| 2015/0051721 A1 | 2/2015 | Cheng |
| 2015/0065213 A1 | 3/2015 | Dugan |
| 2015/0073814 A1 | 3/2015 | Linebaugh |
| 2015/0088544 A1 | 3/2015 | Goldberg |
| 2015/0094192 A1 | 4/2015 | Skwortsow et al. |
| 2015/0099458 A1 | 4/2015 | Weisner et al. |
| 2015/0099952 A1 | 4/2015 | Lain et al. |
| 2015/0111644 A1 | 4/2015 | Larson |
| 2015/0112230 A1 | 4/2015 | Iglesias |
| 2015/0112702 A1 | 4/2015 | Joao et al. |
| 2015/0130830 A1 | 5/2015 | Nagasaki |
| 2015/0141200 A1 | 5/2015 | Murray et al. |
| 2015/0142142 A1 | 5/2015 | Campana Aguilera et al. |
| 2015/0149217 A1 | 5/2015 | Kaburagi |
| 2015/0151162 A1 | 6/2015 | Dugan |
| 2015/0157938 A1 | 6/2015 | Domansky et al. |
| 2015/0161331 A1 | 6/2015 | Oleynik |
| 2015/0161876 A1 | 6/2015 | Castillo |
| 2015/0174446 A1 | 6/2015 | Chiang |
| 2015/0196805 A1 | 7/2015 | Koduri |
| 2015/0217056 A1 | 8/2015 | Kadavy et al. |
| 2015/0251074 A1 | 9/2015 | Ahmed et al. |
| 2015/0257679 A1 | 9/2015 | Ross |
| 2015/0265209 A1 | 9/2015 | Zhang |
| 2015/0290061 A1 | 10/2015 | Stafford et al. |
| 2015/0339442 A1 | 11/2015 | Oleynik |
| 2015/0341812 A1 | 11/2015 | Dion et al. |
| 2015/0351664 A1 | 12/2015 | Ross |
| 2015/0351665 A1 | 12/2015 | Ross |
| 2015/0360069 A1 | 12/2015 | Marti et al. |
| 2015/0379232 A1 | 12/2015 | Mainwaring et al. |
| 2015/0379430 A1 | 12/2015 | Dirac et al. |
| 2016/0004820 A1 | 1/2016 | Moore |
| 2016/0007885 A1 | 1/2016 | Basta et al. |
| 2016/0015995 A1 | 1/2016 | Leung et al. |
| 2016/0023081 A1 | 1/2016 | Popa-Simil et al. |
| 2016/0045170 A1 | 2/2016 | Migita |
| 2016/0096073 A1 | 4/2016 | Rahman et al. |
| 2016/0117471 A1 | 4/2016 | Belt et al. |
| 2016/0132643 A1 | 5/2016 | Radhakrishna et al. |
| 2016/0140319 A1 | 5/2016 | Stark |
| 2016/0143593 A1 | 5/2016 | Fu et al. |
| 2016/0151670 A1 | 6/2016 | Dugan |
| 2016/0158534 A1 | 6/2016 | Guarraia et al. |
| 2016/0166833 A1 | 6/2016 | Bum |
| 2016/0166881 A1 | 6/2016 | Ridgel et al. |
| 2016/0193306 A1 | 7/2016 | Rabovsky et al. |
| 2016/0197918 A1 | 7/2016 | Turgeman et al. |
| 2016/0213924 A1 | 7/2016 | Coleman |
| 2016/0275259 A1 | 9/2016 | Nolan et al. |
| 2016/0287166 A1 | 10/2016 | Tran |
| 2016/0302666 A1 | 10/2016 | Shaya |
| 2016/0302721 A1 | 10/2016 | Wiedenhoefer et al. |
| 2016/0317869 A1 | 11/2016 | Dugan |
| 2016/0322078 A1 | 11/2016 | Bose et al. |
| 2016/0325140 A1 | 11/2016 | Wu |
| 2016/0332028 A1 | 11/2016 | Melnik |
| 2016/0345841 A1 | 12/2016 | Jang et al. |
| 2016/0354636 A1 | 12/2016 | Jang |
| 2016/0361025 A1 | 12/2016 | Reicher et al. |
| 2016/0361597 A1 | 12/2016 | Cole et al. |
| 2016/0373477 A1 | 12/2016 | Moyle |
| 2017/0004260 A1 | 1/2017 | Moturu et al. |
| 2017/0011179 A1 | 1/2017 | Arshad et al. |
| 2017/0032092 A1 | 2/2017 | Mink et al. |
| 2017/0033375 A1 | 2/2017 | Ohmori et al. |
| 2017/0042467 A1 | 2/2017 | Herr et al. |
| 2017/0046488 A1 | 2/2017 | Pereira |
| 2017/0065851 A1 | 3/2017 | Deluca et al. |
| 2017/0080320 A1 | 3/2017 | Smith |
| 2017/0091422 A1 | 3/2017 | Kumar et al. |
| 2017/0095670 A1 | 4/2017 | Ghaffari et al. |
| 2017/0095692 A1 | 4/2017 | Chang et al. |
| 2017/0095693 A1 | 4/2017 | Chang et al. |
| 2017/0100637 A1 | 4/2017 | Princen et al. |
| 2017/0106242 A1 | 4/2017 | Dugan |
| 2017/0113092 A1 | 4/2017 | Johnson |
| 2017/0128769 A1 | 5/2017 | Long et al. |
| 2017/0132947 A1 | 5/2017 | Maeda et al. |
| 2017/0136296 A1 | 5/2017 | Barrera et al. |
| 2017/0143261 A1 | 5/2017 | Wiedenhoefer et al. |
| 2017/0147752 A1 | 5/2017 | Toru |
| 2017/0147789 A1 | 5/2017 | Wiedenhoefer et al. |
| 2017/0148297 A1 | 5/2017 | Ross |
| 2017/0168555 A1 | 6/2017 | Munoz et al. |
| 2017/0181698 A1 | 6/2017 | Wiedenhoefer et al. |
| 2017/0190052 A1 | 7/2017 | Jaekel et al. |
| 2017/0202724 A1 | 7/2017 | De Rossi |
| 2017/0209766 A1 | 7/2017 | Riley et al. |
| 2017/0220751 A1 | 8/2017 | Davis |
| 2017/0228517 A1 | 8/2017 | Saliman et al. |
| 2017/0235882 A1 | 8/2017 | Orlov et al. |
| 2017/0235906 A1 | 8/2017 | Dorris et al. |
| 2017/0243028 A1 | 8/2017 | LaFever et al. |
| 2017/0258370 A1 | 9/2017 | Plotnik-Peleg et al. |
| 2017/0262604 A1 | 9/2017 | Francois |
| 2017/0265800 A1 | 9/2017 | Auchinleck et al. |
| 2017/0266501 A1 | 9/2017 | Sanders et al. |
| 2017/0270260 A1 | 9/2017 | Shetty |
| 2017/0278209 A1 | 9/2017 | Olsen et al. |
| 2017/0282015 A1 | 10/2017 | Wicks et al. |
| 2017/0283508 A1 | 10/2017 | Demopulos et al. |
| 2017/0286621 A1 | 10/2017 | Cox |
| 2017/0296861 A1 | 10/2017 | Burkinshaw |
| 2017/0300654 A1 | 10/2017 | Stein et al. |
| 2017/0304024 A1 | 10/2017 | Nobrega |
| 2017/0312614 A1 | 11/2017 | Tran et al. |
| 2017/0323481 A1 | 11/2017 | Tran et al. |
| 2017/0329917 A1 | 11/2017 | McRaith et al. |
| 2017/0329933 A1 | 11/2017 | Brust |
| 2017/0333755 A1 | 11/2017 | Rider |
| 2017/0337033 A1 | 11/2017 | Duyan et al. |
| 2017/0337334 A1 | 11/2017 | Stanczak |
| 2017/0344726 A1 | 11/2017 | Duffy et al. |
| 2017/0347923 A1 | 12/2017 | Roh |

(56) References Cited

U.S. PATENT DOCUMENTS

| | | |
|---|---|---|
| 2017/0360586 A1 | 12/2017 | Dempers et al. |
| 2017/0368413 A1 | 12/2017 | Shavit |
| 2018/0017806 A1 | 1/2018 | Wang et al. |
| 2018/0036591 A1 | 2/2018 | King et al. |
| 2018/0036593 A1 | 2/2018 | Ridgel et al. |
| 2018/0052962 A1 | 2/2018 | Van Der Koijk et al. |
| 2018/0056104 A1 | 3/2018 | Cromie et al. |
| 2018/0056130 A1 | 3/2018 | Bitran et al. |
| 2018/0060494 A1 | 3/2018 | Dias et al. |
| 2018/0071565 A1 | 3/2018 | Gomberg et al. |
| 2018/0071566 A1 | 3/2018 | Gomberg et al. |
| 2018/0071569 A1 | 3/2018 | Gomberg et al. |
| 2018/0071570 A1 | 3/2018 | Gomberg et al. |
| 2018/0071571 A1 | 3/2018 | Gomberg et al. |
| 2018/0071572 A1 | 3/2018 | Gomberg et al. |
| 2018/0075205 A1 | 3/2018 | Moturu et al. |
| 2018/0078843 A1 | 3/2018 | Tran et al. |
| 2018/0085615 A1 | 3/2018 | Astolfi et al. |
| 2018/0096111 A1 | 4/2018 | Wells et al. |
| 2018/0099178 A1 | 4/2018 | Schaefer et al. |
| 2018/0102190 A1 | 4/2018 | Hogue et al. |
| 2018/0113985 A1 | 4/2018 | Gandy et al. |
| 2018/0116741 A1 | 5/2018 | Garcia Kilroy et al. |
| 2018/0117417 A1 | 5/2018 | Davis |
| 2018/0130555 A1 | 5/2018 | Chronis et al. |
| 2018/0140927 A1 | 5/2018 | Kito |
| 2018/0146870 A1 | 5/2018 | Shemesh |
| 2018/0177612 A1 | 6/2018 | Trabish et al. |
| 2018/0178061 A1 | 6/2018 | O'larte et al. |
| 2018/0199855 A1 | 7/2018 | Odame et al. |
| 2018/0200577 A1 | 7/2018 | Dugan |
| 2018/0220935 A1 | 8/2018 | Tadano et al. |
| 2018/0228682 A1 | 8/2018 | Bayerlein et al. |
| 2018/0232492 A1 | 8/2018 | Al-Alul et al. |
| 2018/0236307 A1 | 8/2018 | Hyde et al. |
| 2018/0240552 A1 | 8/2018 | Tuyl et al. |
| 2018/0253991 A1 | 9/2018 | Tang et al. |
| 2018/0255110 A1 | 9/2018 | Dowlatkhah et al. |
| 2018/0256079 A1 | 9/2018 | Yang et al. |
| 2018/0263530 A1 | 9/2018 | Jung |
| 2018/0263535 A1 | 9/2018 | Cramer |
| 2018/0263552 A1 | 9/2018 | Graman et al. |
| 2018/0264312 A1 | 9/2018 | Pompile et al. |
| 2018/0271432 A1 | 9/2018 | Auchinleck et al. |
| 2018/0272184 A1 | 9/2018 | Vassilaros et al. |
| 2018/0280784 A1 | 10/2018 | Romeo et al. |
| 2018/0296143 A1 | 10/2018 | Anderson et al. |
| 2018/0296157 A1 | 10/2018 | Bleich et al. |
| 2018/0318122 A1 | 11/2018 | LeCursi et al. |
| 2018/0326243 A1 | 11/2018 | Badi et al. |
| 2018/0330058 A1 | 11/2018 | Bates |
| 2018/0330810 A1 | 11/2018 | Gamarnik |
| 2018/0330824 A1 | 11/2018 | Athey et al. |
| 2018/0290017 A1 | 12/2018 | Fung |
| 2018/0353812 A1 | 12/2018 | Lannon et al. |
| 2018/0360340 A1 | 12/2018 | Rehse et al. |
| 2018/0366225 A1* | 12/2018 | Mansi .................. H04L 67/12 |
| 2018/0373844 A1 | 12/2018 | Ferrandez-Escamez et al. |
| 2019/0009135 A1 | 1/2019 | Wu |
| 2019/0019163 A1 | 1/2019 | Batey et al. |
| 2019/0019573 A1 | 1/2019 | Lake et al. |
| 2019/0019578 A1 | 1/2019 | Vaccaro |
| 2019/0030415 A1 | 1/2019 | Volpe, Jr. |
| 2019/0031284 A1 | 1/2019 | Fuchs |
| 2019/0046794 A1 | 2/2019 | Goodall et al. |
| 2019/0060708 A1 | 2/2019 | Fung |
| 2019/0065970 A1 | 2/2019 | Bonutti et al. |
| 2019/0066832 A1 | 2/2019 | Kang et al. |
| 2019/0076701 A1 | 3/2019 | Dugan |
| 2019/0080802 A1 | 3/2019 | Ziobro et al. |
| 2019/0083846 A1 | 3/2019 | Eder |
| 2019/0088356 A1 | 3/2019 | Oliver et al. |
| 2019/0090744 A1 | 3/2019 | Mahfouz |
| 2019/0096534 A1 | 3/2019 | Joao |
| 2019/0105551 A1 | 4/2019 | Ray |
| 2019/0111299 A1 | 4/2019 | Radcliffe et al. |
| 2019/0115097 A1 | 4/2019 | Macoviak et al. |
| 2019/0117156 A1 | 4/2019 | Howard et al. |
| 2019/0118038 A1 | 4/2019 | Tana et al. |
| 2019/0126099 A1 | 5/2019 | Hoang |
| 2019/0132948 A1 | 5/2019 | Longinotti-Buitoni et al. |
| 2019/0134454 A1 | 5/2019 | Mahoney et al. |
| 2019/0137988 A1 | 5/2019 | Cella et al. |
| 2019/0143191 A1 | 5/2019 | Ran et al. |
| 2019/0145774 A1 | 5/2019 | Ellis |
| 2019/0163876 A1 | 5/2019 | Remme et al. |
| 2019/0167988 A1 | 6/2019 | Shahriari et al. |
| 2019/0172587 A1 | 6/2019 | Park et al. |
| 2019/0175988 A1 | 6/2019 | Volterrani et al. |
| 2019/0183715 A1 | 6/2019 | Kapure et al. |
| 2019/0200920 A1 | 7/2019 | Tien et al. |
| 2019/0209891 A1 | 7/2019 | Fung |
| 2019/0214119 A1 | 7/2019 | Wachira et al. |
| 2019/0223797 A1 | 7/2019 | Tran |
| 2019/0224528 A1 | 7/2019 | Omid-Zohoor et al. |
| 2019/0228856 A1 | 7/2019 | Leifer |
| 2019/0232108 A1 | 8/2019 | Kovach et al. |
| 2019/0240103 A1 | 8/2019 | Hepler et al. |
| 2019/0240541 A1 | 8/2019 | Denton et al. |
| 2019/0244540 A1 | 8/2019 | Errante et al. |
| 2019/0251456 A1 | 8/2019 | Constantin |
| 2019/0261959 A1 | 8/2019 | Frankel |
| 2019/0262084 A1 | 8/2019 | Roh |
| 2019/0269343 A1 | 9/2019 | Ramos Murguialday et al. |
| 2019/0274523 A1 | 9/2019 | Bates et al. |
| 2019/0275368 A1 | 9/2019 | Maroldi |
| 2019/0304584 A1 | 10/2019 | Savolainen |
| 2019/0307983 A1 | 10/2019 | Goldman |
| 2019/0314681 A1 | 10/2019 | Yang |
| 2019/0344123 A1 | 11/2019 | Rubin et al. |
| 2019/0354632 A1 | 11/2019 | Mital et al. |
| 2019/0362242 A1 | 11/2019 | Pillai et al. |
| 2019/0366146 A1 | 12/2019 | Tong et al. |
| 2019/0385199 A1 | 12/2019 | Bender et al. |
| 2019/0388728 A1 | 12/2019 | Wang et al. |
| 2019/0392936 A1 | 12/2019 | Arric et al. |
| 2019/0392939 A1 | 12/2019 | Basta et al. |
| 2020/0005928 A1 | 1/2020 | Daniel |
| 2020/0034707 A1 | 1/2020 | Kivatinos et al. |
| 2020/0038703 A1 | 2/2020 | Cleary et al. |
| 2020/0051446 A1 | 2/2020 | Rubinstein et al. |
| 2020/0066390 A1 | 2/2020 | Svendrys et al. |
| 2020/0085300 A1 | 3/2020 | Kwatra et al. |
| 2020/0090802 A1 | 3/2020 | Maron |
| 2020/0093418 A1 | 3/2020 | Kluger et al. |
| 2020/0143922 A1 | 5/2020 | Chekroud et al. |
| 2020/0151595 A1 | 5/2020 | Jayalath et al. |
| 2020/0151646 A1 | 5/2020 | De La Fuente Sanchez |
| 2020/0152339 A1 | 5/2020 | Pulitzer et al. |
| 2020/0160198 A1 | 5/2020 | Reeves et al. |
| 2020/0170876 A1 | 6/2020 | Kapure et al. |
| 2020/0176098 A1 | 6/2020 | Lucas et al. |
| 2020/0197744 A1 | 6/2020 | Schweighofer |
| 2020/0221975 A1 | 7/2020 | Basta et al. |
| 2020/0237291 A1 | 7/2020 | Raja |
| 2020/0237452 A1 | 7/2020 | Wolf et al. |
| 2020/0267487 A1 | 8/2020 | Siva |
| 2020/0275886 A1 | 9/2020 | Mason |
| 2020/0289045 A1 | 9/2020 | Hacking et al. |
| 2020/0289046 A1 | 9/2020 | Hacking et al. |
| 2020/0289879 A1 | 9/2020 | Hacking et al. |
| 2020/0289880 A1 | 9/2020 | Hacking et al. |
| 2020/0289881 A1 | 9/2020 | Hacking et al. |
| 2020/0289889 A1 | 9/2020 | Hacking et al. |
| 2020/0293712 A1 | 9/2020 | Potts et al. |
| 2020/0303063 A1 | 9/2020 | Sharma et al. |
| 2020/0312447 A1 | 10/2020 | Bohn et al. |
| 2020/0334972 A1 | 10/2020 | Gopalakrishnan |
| 2020/0353314 A1 | 11/2020 | Messinger |
| 2020/0357299 A1 | 11/2020 | Patel et al. |
| 2020/0365256 A1 | 11/2020 | Hayashitani et al. |
| 2020/0395112 A1 | 12/2020 | Ronner |
| 2020/0398083 A1 | 12/2020 | Al-Alul et al. |
| 2020/0401224 A1 | 12/2020 | Cotton |

(56) References Cited

U.S. PATENT DOCUMENTS

| | | |
|---|---|---|
| 2020/0402662 A1 | 12/2020 | Esmailian et al. |
| 2020/0410374 A1 | 12/2020 | White |
| 2020/0410385 A1 | 12/2020 | Otsuki |
| 2020/0411162 A1 | 12/2020 | Lien et al. |
| 2021/0005224 A1 | 1/2021 | Rothschild et al. |
| 2021/0005319 A1 | 1/2021 | Otsuki et al. |
| 2021/0008413 A1 | 1/2021 | Asikainen et al. |
| 2021/0015560 A1 | 1/2021 | Boddington et al. |
| 2021/0027889 A1 | 1/2021 | Neil et al. |
| 2021/0035674 A1 | 2/2021 | Volosin et al. |
| 2021/0050086 A1 | 2/2021 | Rose et al. |
| 2021/0065855 A1 | 3/2021 | Pepin et al. |
| 2021/0074178 A1 | 3/2021 | Ilan et al. |
| 2021/0076981 A1 | 3/2021 | Hacking et al. |
| 2021/0077860 A1 | 3/2021 | Posnack et al. |
| 2021/0077884 A1 | 3/2021 | De Las Casas Zolezzi et al. |
| 2021/0082554 A1 | 3/2021 | Kalia et al. |
| 2021/0093891 A1 | 4/2021 | Sheng |
| 2021/0098129 A1 | 4/2021 | Neumann |
| 2021/0101051 A1 | 4/2021 | Posnack et al. |
| 2021/0113890 A1 | 4/2021 | Posnack et al. |
| 2021/0125696 A1 | 4/2021 | Liu et al. |
| 2021/0127974 A1 | 5/2021 | Mason et al. |
| 2021/0128080 A1 | 5/2021 | Mason et al. |
| 2021/0128255 A1 | 5/2021 | Mason et al. |
| 2021/0128978 A1 | 5/2021 | Gilstrom et al. |
| 2021/0134412 A1 | 5/2021 | Guaneri et al. |
| 2021/0134425 A1 | 5/2021 | Mason et al. |
| 2021/0134428 A1 | 5/2021 | Mason et al. |
| 2021/0134430 A1 | 5/2021 | Mason et al. |
| 2021/0134432 A1 | 5/2021 | Mason et al. |
| 2021/0134456 A1 | 5/2021 | Posnack et al. |
| 2021/0134457 A1 | 5/2021 | Mason et al. |
| 2021/0134458 A1 | 5/2021 | Mason et al. |
| 2021/0134463 A1 | 5/2021 | Mason et al. |
| 2021/0138304 A1 | 5/2021 | Mason et al. |
| 2021/0142875 A1 | 5/2021 | Mason et al. |
| 2021/0142893 A1 | 5/2021 | Guaneri et al. |
| 2021/0142898 A1 | 5/2021 | Mason et al. |
| 2021/0142903 A1 | 5/2021 | Mason et al. |
| 2021/0144074 A1 | 5/2021 | Guaneri et al. |
| 2021/0186419 A1 | 6/2021 | Van Ee et al. |
| 2021/0187348 A1 | 6/2021 | Phillips et al. |
| 2021/0202090 A1 | 7/2021 | ODonovan et al. |
| 2021/0202103 A1 | 7/2021 | Bostic et al. |
| 2021/0236020 A1 | 8/2021 | Matijevich et al. |
| 2021/0244998 A1 | 8/2021 | Hacking et al. |
| 2021/0245003 A1 | 8/2021 | Turner |
| 2021/0251562 A1 | 8/2021 | Jain |
| 2021/0272677 A1 | 9/2021 | Barbee |
| 2021/0338469 A1 | 11/2021 | Dempers |
| 2021/0343384 A1 | 11/2021 | Purushothaman et al. |
| 2021/0345879 A1 | 11/2021 | Mason et al. |
| 2021/0345975 A1 | 11/2021 | Mason et al. |
| 2021/0350888 A1 | 11/2021 | Guaneri et al. |
| 2021/0350898 A1 | 11/2021 | Mason et al. |
| 2021/0350899 A1 | 11/2021 | Mason et al. |
| 2021/0350901 A1 | 11/2021 | Mason et al. |
| 2021/0350902 A1 | 11/2021 | Mason et al. |
| 2021/0350914 A1 | 11/2021 | Guaneri et al. |
| 2021/0350926 A1 | 11/2021 | Mason et al. |
| 2021/0361514 A1 | 11/2021 | Choi et al. |
| 2021/0366587 A1 | 11/2021 | Mason et al. |
| 2021/0383909 A1 | 12/2021 | Mason et al. |
| 2021/0391091 A1 | 12/2021 | Mason |
| 2021/0398668 A1 | 12/2021 | Chock et al. |
| 2021/0407670 A1 | 12/2021 | Mason et al. |
| 2021/0407681 A1 | 12/2021 | Mason et al. |
| 2022/0000556 A1 | 1/2022 | Casey et al. |
| 2022/0015838 A1 | 1/2022 | Posnack et al. |
| 2022/0016480 A1 | 1/2022 | Bissonnette et al. |
| 2022/0016482 A1 | 1/2022 | Bissonnette |
| 2022/0016485 A1 | 1/2022 | Bissonnette et al. |
| 2022/0016486 A1 | 1/2022 | Bissonnette |
| 2022/0020469 A1 | 1/2022 | Tanner |
| 2022/0044806 A1 | 2/2022 | Sanders et al. |
| 2022/0047921 A1 | 2/2022 | Bissonnette et al. |
| 2022/0079690 A1 | 3/2022 | Mason et al. |
| 2022/0080256 A1 | 3/2022 | Arn et al. |
| 2022/0080265 A1 | 3/2022 | Watterson |
| 2022/0105384 A1 | 4/2022 | Hacking et al. |
| 2022/0105385 A1 | 4/2022 | Hacking et al. |
| 2022/0105390 A1 | 4/2022 | Yuasa |
| 2022/0115133 A1 | 4/2022 | Mason et al. |
| 2022/0118218 A1 | 4/2022 | Bense et al. |
| 2022/0122724 A1 | 4/2022 | Durlach et al. |
| 2022/0126169 A1 | 4/2022 | Mason |
| 2022/0133576 A1 | 5/2022 | Choi et al. |
| 2022/0148725 A1 | 5/2022 | Mason et al. |
| 2022/0176039 A1 | 6/2022 | Lintereur et al. |
| 2022/0181004 A1 | 6/2022 | Zilca et al. |
| 2022/0193491 A1 | 6/2022 | Mason et al. |
| 2022/0230729 A1 | 7/2022 | Mason |
| 2022/0238222 A1 | 7/2022 | Neuberg |
| 2022/0238223 A1 | 7/2022 | Mason et al. |
| 2022/0258935 A1 | 8/2022 | Kraft |
| 2022/0262483 A1 | 8/2022 | Rosenberg et al. |
| 2022/0262504 A1 | 8/2022 | Bratty et al. |
| 2022/0266094 A1 | 8/2022 | Mason et al. |
| 2022/0270738 A1 | 8/2022 | Mason et al. |
| 2022/0273985 A1 | 9/2022 | Jeong et al. |
| 2022/0273986 A1 | 9/2022 | Mason |
| 2022/0288460 A1 | 9/2022 | Mason |
| 2022/0288461 A1 | 9/2022 | Ashley et al. |
| 2022/0288462 A1 | 9/2022 | Ashley et al. |
| 2022/0293257 A1 | 9/2022 | Guaneri et al. |
| 2022/0300787 A1 | 9/2022 | Wall et al. |
| 2022/0304881 A1 | 9/2022 | Choi et al. |
| 2022/0304882 A1 | 9/2022 | Choi |
| 2022/0305328 A1 | 9/2022 | Choi et al. |
| 2022/0314072 A1 | 10/2022 | Bissonnette et al. |
| 2022/0314075 A1 | 10/2022 | Mason et al. |
| 2022/0323826 A1 | 10/2022 | Khurana |
| 2022/0327714 A1 | 10/2022 | Cook et al. |
| 2022/0327807 A1 | 10/2022 | Cook et al. |
| 2022/0328181 A1 | 10/2022 | Mason et al. |
| 2022/0330823 A1 | 10/2022 | Janssen |
| 2022/0331663 A1 | 10/2022 | Mason |
| 2022/0338761 A1 | 10/2022 | Maddahi et al. |
| 2022/0339052 A1 | 10/2022 | Kim |
| 2022/0339501 A1 | 10/2022 | Mason et al. |
| 2022/0370851 A1 | 11/2022 | Guidarelli et al. |
| 2022/0384012 A1 | 12/2022 | Mason |
| 2022/0392591 A1 | 12/2022 | Guaneri et al. |
| 2022/0395232 A1 | 12/2022 | Locke |
| 2022/0401783 A1 | 12/2022 | Choi |
| 2022/0415469 A1 | 12/2022 | Mason |
| 2022/0415471 A1 | 12/2022 | Mason |
| 2023/0001268 A1 | 1/2023 | Bissonnette et al. |
| 2023/0013530 A1 | 1/2023 | Mason |
| 2023/0014598 A1 | 1/2023 | Mason et al. |
| 2023/0029639 A1 | 2/2023 | Roy |
| 2023/0047253 A1 | 2/2023 | Gnanasambandam et al. |
| 2023/0048040 A1 | 2/2023 | Hacking et al. |
| 2023/0051751 A1 | 2/2023 | Hacking et al. |
| 2023/0058605 A1 | 2/2023 | Mason |
| 2023/0060039 A1 | 2/2023 | Mason |
| 2023/0072368 A1 | 3/2023 | Mason |
| 2023/0078793 A1 | 3/2023 | Mason |
| 2023/0119461 A1 | 4/2023 | Mason |
| 2023/0190100 A1 | 6/2023 | Stump |
| 2023/0201656 A1 | 6/2023 | Hacking et al. |
| 2023/0207097 A1 | 6/2023 | Mason |
| 2023/0207124 A1 | 6/2023 | Walsh et al. |
| 2023/0215539 A1 | 7/2023 | Rosenberg et al. |
| 2023/0215552 A1 | 7/2023 | Khotilovich et al. |
| 2023/0218950 A1 | 7/2023 | Belson et al. |
| 2023/0245747 A1 | 8/2023 | Rosenberg et al. |
| 2023/0245748 A1 | 8/2023 | Rosenberg et al. |
| 2023/0245750 A1 | 8/2023 | Rosenberg et al. |
| 2023/0245751 A1 | 8/2023 | Rosenberg et al. |
| 2023/0253089 A1 | 8/2023 | Rosenberg et al. |
| 2023/0255555 A1 | 8/2023 | Sundaram et al. |
| 2023/0263428 A1 | 8/2023 | Hull et al. |

(56) References Cited

U.S. PATENT DOCUMENTS

| | | |
|---|---|---|
| 2023/0274813 A1 | 8/2023 | Rosenberg et al. |
| 2023/0282329 A1 | 9/2023 | Mason et al. |
| 2023/0364472 A1 | 11/2023 | Posnack |
| 2023/0368886 A1 | 11/2023 | Rosenberg |
| 2023/0377710 A1 | 11/2023 | Chen et al. |
| 2023/0377711 A1 | 11/2023 | Rosenberg |
| 2023/0377712 A1 | 11/2023 | Rosenberg |
| 2023/0386639 A1 | 11/2023 | Rosenberg |
| 2023/0395231 A1 | 12/2023 | Rosenberg |
| 2023/0395232 A1 | 12/2023 | Rosenberg |
| 2024/0029856 A1 | 1/2024 | Rosenberg |

FOREIGN PATENT DOCUMENTS

| | | |
|---|---|---|
| CN | 101964151 A | 2/2011 |
| CN | 201889024 U | 7/2011 |
| CN | 202220794 U | 5/2012 |
| CN | 102670381 A | 9/2012 |
| CN | 103263336 A | 8/2013 |
| CN | 103390357 A | 11/2013 |
| CN | 103473631 A | 12/2013 |
| CN | 103488880 A | 1/2014 |
| CN | 103501328 A | 1/2014 |
| CN | 103721343 A | 4/2014 |
| CN | 203677851 U | 7/2014 |
| CN | 104335211 A | 2/2015 |
| CN | 105620643 A | 6/2016 |
| CN | 105683977 A | 6/2016 |
| CN | 103136447 B | 8/2016 |
| CN | 105894088 A | 8/2016 |
| CN | 105930668 A | 9/2016 |
| CN | 205626871 U | 10/2016 |
| CN | 106127646 A | 11/2016 |
| CN | 106236502 A | 12/2016 |
| CN | 106510985 A | 3/2017 |
| CN | 106621195 A | 5/2017 |
| CN | 107066819 A | 8/2017 |
| CN | 107430641 A | 12/2017 |
| CN | 107551475 A | 1/2018 |
| CN | 107736982 A | 2/2018 |
| CN | 107930021 A | 4/2018 |
| CN | 108078737 A | 5/2018 |
| CN | 208224811 U | 12/2018 |
| CN | 109191954 A | 1/2019 |
| CN | 109363887 A | 2/2019 |
| CN | 208573971 U | 3/2019 |
| CN | 110148472 A | 8/2019 |
| CN | 110201358 A | 9/2019 |
| CN | 110215188 A | 9/2019 |
| CN | 110322957 A | 10/2019 |
| CN | 110808092 A | 2/2020 |
| CN | 110931103 A | 3/2020 |
| CN | 110993057 A | 4/2020 |
| CN | 111105859 A | 5/2020 |
| CN | 111111110 A | 5/2020 |
| CN | 111370088 A | 7/2020 |
| CN | 111460305 A | 7/2020 |
| CN | 111790111 A | 10/2020 |
| CN | 112071393 A | 12/2020 |
| CN | 212141371 U | 12/2020 |
| CN | 112289425 A | 1/2021 |
| CN | 212624809 U | 2/2021 |
| CN | 112603295 A | 4/2021 |
| CN | 213190965 U | 5/2021 |
| CN | 113384850 A | 9/2021 |
| CN | 113499572 A | 10/2021 |
| CN | 215136488 U | 12/2021 |
| CN | 113885361 A | 1/2022 |
| CN | 114049961 A | 2/2022 |
| CN | 114203274 A | 3/2022 |
| CN | 216258145 U | 4/2022 |
| CN | 114632302 A | 6/2022 |
| CN | 114694824 A | 7/2022 |
| CN | 114898832 A | 8/2022 |
| CN | 114983760 A | 9/2022 |
| CN | 217472652 U | 9/2022 |
| CN | 110270062 B | 10/2022 |
| CN | 218420859 U | 2/2023 |
| CN | 115954081 A | 4/2023 |
| DE | 95019 C | 1/1897 |
| DE | 7628633 U1 | 12/1977 |
| DE | 8519150 U1 | 10/1985 |
| DE | 3732905 A1 | 7/1988 |
| DE | 19619820 A1 | 12/1996 |
| DE | 29620008 U1 | 2/1997 |
| DE | 19947926 A1 | 4/2001 |
| DE | 102018202497 A1 | 8/2018 |
| DE | 102018211212 A1 | 1/2019 |
| DE | 102019108425 B3 | 8/2020 |
| EP | 199600 A2 | 10/1986 |
| EP | 0383137 A2 | 8/1990 |
| EP | 634319 A2 | 1/1995 |
| EP | 0919259 A1 | 6/1999 |
| EP | 1034817 A1 | 9/2000 |
| EP | 1159989 A1 | 12/2001 |
| EP | 1391179 A1 | 2/2004 |
| EP | 1968028 | 9/2008 |
| EP | 2564904 A1 | 3/2013 |
| EP | 2575064 A1 | 4/2013 |
| EP | 1909730 B1 | 4/2014 |
| EP | 2815242 A4 | 12/2014 |
| EP | 2869805 A | 5/2015 |
| EP | 2997951 A1 | 3/2016 |
| EP | 2688472 B1 | 4/2016 |
| EP | 3264303 A1 | 1/2018 |
| EP | 3323473 A1 | 5/2018 |
| EP | 3547322 A1 | 10/2019 |
| EP | 3627514 A1 | 3/2020 |
| EP | 3671700 A1 | 6/2020 |
| EP | 3688537 A1 | 8/2020 |
| EP | 3731733 A1 | 11/2020 |
| EP | 3984508 A1 | 4/2022 |
| EP | 3984509 A1 | 4/2022 |
| EP | 3984510 A1 | 4/2022 |
| EP | 3984511 A1 | 4/2022 |
| EP | 3984512 A1 | 4/2022 |
| EP | 3984513 A1 | 4/2022 |
| EP | 4054699 A1 | 9/2022 |
| EP | 4112033 A1 | 1/2023 |
| FR | 2527541 A2 | 12/1983 |
| FR | 3127393 A1 | 3/2023 |
| GB | 141664 A | 11/1920 |
| GB | 2336140 A | 10/1999 |
| GB | 2372459 A | 8/2002 |
| GB | 2512431 A | 10/2014 |
| GB | 2591542 B | 3/2022 |
| IN | 201811043670 A | 7/2018 |
| JP | 2000005339 A | 1/2000 |
| JP | 2003225875 A | 8/2003 |
| JP | 2005227928 A | 8/2005 |
| JP | 2005227928 A1 | 8/2005 |
| JP | 2009112336 A | 5/2009 |
| JP | 2013515995 A | 5/2013 |
| JP | 2014104139 A | 6/2014 |
| JP | 3193662 U | 10/2014 |
| JP | 3198173 U | 6/2015 |
| JP | 5804063 B2 | 11/2015 |
| JP | 2018102842 A | 7/2018 |
| JP | 2019028647 A | 2/2019 |
| JP | 2019134909 A | 8/2019 |
| JP | 6573739 B1 | 9/2019 |
| JP | 6659831 B2 | 3/2020 |
| JP | 2020057082 A | 4/2020 |
| JP | 6710357 B1 | 6/2020 |
| JP | 6775757 B1 | 10/2020 |
| JP | 2021027917 A | 2/2021 |
| JP | 6871379 B2 | 5/2021 |
| JP | 2022521378 A | 4/2022 |
| JP | 3238491 U | 7/2022 |
| JP | 7198364 B2 | 12/2022 |
| JP | 7202474 B2 | 1/2023 |
| JP | 7231750 B2 | 3/2023 |
| JP | 7231751 B2 | 3/2023 |
| JP | 7231752 B2 | 3/2023 |

(56) References Cited

FOREIGN PATENT DOCUMENTS

| | | |
|---|---|---|
| KR | 20020009724 A | 2/2002 |
| KR | 200276919 Y1 | 5/2002 |
| KR | 20020065253 A | 8/2002 |
| KR | 100582596 B1 | 5/2006 |
| KR | 101042258 B1 | 6/2011 |
| KR | 101258250 B1 | 4/2013 |
| KR | 101325581 B1 | 11/2013 |
| KR | 20140128630 A | 11/2014 |
| KR | 20150017693 A | 2/2015 |
| KR | 20150078191 A | 7/2015 |
| KR | 101580071 B1 | 12/2015 |
| KR | 101647620 B1 | 8/2016 |
| KR | 20160093990 A | 8/2016 |
| KR | 20170038837 A | 4/2017 |
| KR | 20180004928 A | 1/2018 |
| KR | 20190029175 A | 3/2019 |
| KR | 20190056116 A | 5/2019 |
| KR | 101988167 B1 | 6/2019 |
| KR | 101969392 B1 | 8/2019 |
| KR | 102055279 B1 | 12/2019 |
| KR | 102088333 B1 | 3/2020 |
| KR | 20200025290 A | 3/2020 |
| KR | 20200029180 A | 3/2020 |
| KR | 102097190 B1 | 4/2020 |
| KR | 102116664 B1 | 5/2020 |
| KR | 102116968 B1 | 5/2020 |
| KR | 20200056233 A | 5/2020 |
| KR | 102120828 B1 | 6/2020 |
| KR | 102121586 B1 | 6/2020 |
| KR | 102142713 B1 | 8/2020 |
| KR | 102162522 B1 | 10/2020 |
| KR | 20200119665 A | 10/2020 |
| KR | 102173553 B1 | 11/2020 |
| KR | 102180079 B1 | 11/2020 |
| KR | 102188766 B1 | 12/2020 |
| KR | 102196793 B1 | 12/2020 |
| KR | 20210006212 A | 1/2021 |
| KR | 102224188 B1 | 3/2021 |
| KR | 102224618 B1 | 3/2021 |
| KR | 102246049 B1 | 4/2021 |
| KR | 102246050 B1 | 4/2021 |
| KR | 102246051 B1 | 4/2021 |
| KR | 102246052 B1 | 4/2021 |
| KR | 20210052028 A | 5/2021 |
| KR | 102264498 B1 | 6/2021 |
| KR | 102352602 B1 | 1/2022 |
| KR | 102352603 B1 | 1/2022 |
| KR | 102352604 B1 | 1/2022 |
| KR | 20220004639 A | 1/2022 |
| KR | 102387577 B1 | 4/2022 |
| KR | 102421437 B1 | 7/2022 |
| KR | 20220102207 A | 7/2022 |
| KR | 102427545 B1 | 8/2022 |
| KR | 102467495 B1 | 11/2022 |
| KR | 102467496 B1 | 11/2022 |
| KR | 102469723 B1 | 11/2022 |
| KR | 102471990 B1 | 11/2022 |
| KR | 20220145989 A | 11/2022 |
| KR | 20220156134 A | 11/2022 |
| KR | 102502744 B1 | 2/2023 |
| KR | 20230019349 A | 2/2023 |
| KR | 20230019350 A | 2/2023 |
| KR | 20230026556 A | 2/2023 |
| KR | 20230026668 A | 2/2023 |
| KR | 20230040526 | 3/2023 |
| KR | 20230050506 A | 4/2023 |
| KR | 20230056118 A | 4/2023 |
| KR | 102528503 B1 | 5/2023 |
| KR | 102531930 B1 | 5/2023 |
| KR | 102532766 B1 | 5/2023 |
| KR | 102539190 B1 | 6/2023 |
| RU | 2014131288 A | 2/2016 |
| RU | 2607953 C2 | 1/2017 |
| TW | M474545 U | 3/2014 |
| TW | I442956 B | 7/2014 |
| TW | M638437 U | 3/2023 |
| WO | 1998009687 | 3/1998 |
| WO | 0149235 A2 | 7/2001 |
| WO | 0151083 A2 | 7/2001 |
| WO | 2001050387 A1 | 7/2001 |
| WO | 2001056465 A1 | 8/2001 |
| WO | 02062211 A2 | 8/2002 |
| WO | 02093312 A2 | 11/2002 |
| WO | 2003043494 | 5/2003 |
| WO | 2005018453 A1 | 3/2005 |
| WO | 2006004430 A2 | 1/2006 |
| WO | 2006012694 A1 | 2/2006 |
| WO | 2007102709 A1 | 9/2007 |
| WO | 2008114291 A1 | 9/2008 |
| WO | 2009003170 A1 | 12/2008 |
| WO | 2009008968 A1 | 1/2009 |
| WO | 2011025322 A2 | 3/2011 |
| WO | 2012128801 A1 | 9/2012 |
| WO | 2013002568 A2 | 1/2013 |
| WO | 2023164292 A1 | 3/2013 |
| WO | 2013122839 A1 | 8/2013 |
| WO | 2014011447 A1 | 1/2014 |
| WO | 2014163976 A1 | 10/2014 |
| WO | 2015026744 A1 | 2/2015 |
| WO | 2015065298 A1 | 5/2015 |
| WO | 2015082555 A1 | 6/2015 |
| WO | 2016151364 A1 | 9/2016 |
| WO | 2016154318 A1 | 9/2016 |
| WO | 2017030781 A1 | 2/2017 |
| WO | 2017166074 A1 | 5/2017 |
| WO | 2017091691 A1 | 6/2017 |
| WO | 2017165238 A1 | 9/2017 |
| WO | 2018081795 A1 | 5/2018 |
| WO | 2018171853 A1 | 9/2018 |
| WO | 2019022706 A1 | 1/2019 |
| WO | 2019143940 A1 | 7/2019 |
| WO | 2020075190 A1 | 4/2020 |
| WO | 2020130979 A1 | 6/2020 |
| WO | 2020149815 A2 | 7/2020 |
| WO | 2020229705 A1 | 11/2020 |
| WO | 2020245727 A1 | 12/2020 |
| WO | 2020249855 A1 | 12/2020 |
| WO | 2020252599 A1 | 12/2020 |
| WO | 2020256577 A1 | 12/2020 |
| WO | 2021021447 A1 | 2/2021 |
| WO | 2021022003 A1 | 2/2021 |
| WO | 2021038980 A1 | 3/2021 |
| WO | 2021055427 A1 | 3/2021 |
| WO | 2021061061 A1 | 4/2021 |
| WO | 2021090267 A1 | 5/2021 |
| WO | 2021138620 A1 | 7/2021 |
| WO | 2021216881 A1 | 10/2021 |
| WO | 2021236961 A1 | 11/2021 |
| WO | 2022047006 A1 | 3/2022 |
| WO | 2022092493 A1 | 5/2022 |
| WO | 2022092494 A1 | 5/2022 |
| WO | 2022212883 A1 | 10/2022 |
| WO | 2022212921 A1 | 10/2022 |
| WO | 2022216498 A1 | 10/2022 |
| WO | 2022251420 A1 | 12/2022 |
| WO | 2023008680 A1 | 2/2023 |
| WO | 2023008681 A1 | 2/2023 |
| WO | 2023022319 A1 | 2/2023 |
| WO | 2023022320 A1 | 2/2023 |
| WO | 2023052695 A1 | 4/2023 |
| WO | 2023091496 A1 | 5/2023 |
| WO | 2023215155 A1 | 11/2023 |
| WO | 2023230075 A1 | 11/2023 |
| WO | 2024013267 A1 | 1/2024 |
| WO | 2024107807 A1 | 5/2024 |

OTHER PUBLICATIONS

Androutsou et al., "A Smartphone Application Designed to Engage the Elderly in Home-Based Rehabilitation," Frontiers in Digital Health, Sep. 2020, vol. 2, Article 15, 13 pages.
Silva et al., "SapoFitness: A mobile health application for dietary evaluation," 2011 IEEE 13th International Conference on U e-Health

(56) References Cited

OTHER PUBLICATIONS

Networking, Applications and Services, Columbia, MO, USA, 2011, 6 pages.

Wang et al., "Interactive wearable systems for upper body rehabilitation: a systematic review," Journal of NeuroEngineering and Rehabilitation, 2017, 21 pages.

Marzolini et al., "Eligibility, Enrollment, and Completion of Exercise-Based Cardiac Rehabilitation Following Stroke Rehabilitation: What Are the Barriers?," Physical Therapy, vol. 100, No. 1, 2019, 13 pages.

Nijjar et al., "Randomized Trial of Mindfulness-Based Stress Reduction in Cardiac Patients Eligible for Cardiac Rehabilitation," Scientific Reports, 2019, 12 pages.

Lara et al., "Human-Robot Sensor Interface for Cardiac Rehabilitation," IEEE International Conference on Rehabilitation Robotics, Jul. 2017, 8 pages.

Ishraque et al., "Artificial Intelligence-Based Rehabilitation Therapy Exercise Recommendation System," 2018 IEEE MIT Undergraduate Research Technology Conference (URTC), Cambridge, MA, USA, 2018, 5 pages.

Zakari et al., "Are There Limitations to Exercise Benefits in Peripheral Arterial Disease?," Frontiers in Cardiovascular Medicine, Nov. 2018, vol. 5, Article 173, 12 pages.

You et al., "Including Blood Vasculature into a Game-Theoretic Model of Cancer Dynamics," Games 2019, 10, 13, 22 pages.

Jeong et al., "Computer-assisted upper extremity training using interactive biking exercise (iBikE) platform," Sep. 2012, 34th Annual International Conference of the IEEE EMBS, 5 pages.

Barrett et al., "Artificial intelligence supported patient self-care in chronic heart failure: a paradigm shift from reactive to predictive, preventive and personalised care," EPMA Journal (2019), pp. 445-464.

Oerkild et al., "Home-based cardiac rehabilitation is an attractive alternative to no cardiac rehabilitation for elderly patients with coronary heart disease: results from a randomised clinical trial," BMJ Open Accessible Medical Research, Nov. 22, 2012, pp. 1-9.

Bravo-Escobar et al., "Effectiveness and safety of a home-based cardiac rehabilitation programme of mixed surveillance in patients with ischemic heart disease at moderate cardiovascular risk: A randomised, controlled clinical trial," BMC Cardiovascular Disorders, 2017, pp. 1-11, vol. 17:66.

Thomas et al., "Home-Based Cardiac Rehabilitation," Circulation, 2019, pp. e69-e89, vol. 140.

Thomas et al., "Home-Based Cardiac Rehabilitation," Journal of the American College of Cardiology, Nov. 1, 2019, pp. 133-153, vol. 74.

Thomas et al., "Home-Based Cardiac Rehabilitation," HHS Public Access, Oct. 2, 2020, pp. 1-39.

Dittus et al., "Exercise-Based Oncology Rehabilitation: Leveraging the Cardiac Rehabilitation Model," Journal of Cardiopulmonary Rehabilitation and Prevention, 2015, pp. 130-139, vol. 35.

Chen et al., "Home-based cardiac rehabilitation improves quality of life, aerobic capacity, and readmission rates in patients with chronic heart failure," Medicine, 2018, pp. 1-5 vol. 97:4.

Lima de Melo Ghisi et al., "A systematic review of patient education in cardiac patients: Do they increase knowledge and promote health behavior change?," Patient Education and Counseling, 2014, pp. 1-15.

Fang et al., "Use of Outpatient Cardiac Rehabilitation Among Heart Attack Survivors—20 States and the District of Columbia, 2013 and Four States, 2015," Morbidity and Mortality Weekly Report, vol. 66, No. 33, Aug. 25, 2017, pp. 869-873.

Beene et al., "AI and Care Delivery: Emerging Opportunities for Artificial Intelligence to Transform How Care Is Delivered," Nov. 2019, American Hospital Association, pp. 1-12.

Chrif et al., "Control design for a lower-limb paediatric therapy device using linear motor technology," Article, 2017, pp. 119-127, Science Direct, Switzerland.

Robben et al., "Delta Features From Ambient Sensor Data are Good Predictors of Change in Functional Health," Article, 2016, pp. 2168-2194, vol. 21, No. 4, IEEE Journal of Biomedical and Health Informatics.

Kantoch et al., "Recognition of Sedentary Behavior by Machine Learning Analysis of Wearable Sensors during Activities of Daily Living for Telemedical Assessment of Cardiovascular Risk," Article, 2018, 17 pages, Sensors, Poland.

Warburton et al., "International Launch of the PAR-•Q+ and ePARmed-•X+ Validation of the PAR-•Q+ and ePARmed••X+," Health & Fitness Journal of Canada, 2011, 9 pages, vol. 4, No. 2.

Malloy, Online Article "AI-enabled EKGs find difference between numerical age and biological age significantly affects health, longevity", Website: https://newsnetwork.mayoclinic.org/discussion/ai-enabled-ekgs-find-difference-between-numerical-age-and-biological-age-significantly-affects-health-longevity/, Mayo Clinic News Network, May 20, 2021, retrieved: Jan. 23, 2023, p. 1-4.

Davenport et al., "The Potential for Artificial Intelligence In Healthcare", 2019, Future Healthcare Journal 2019, vol. 6, No. 2: Year: 2019, pp. 1-5.

Ahmed et al., "Artificial Intelligence With Multi-Functional Machine Learning Platform Development for Better Healthcare and Precision Medicine", 2020, Database (Oxford), 2020:baaa010. doi: 10.1093/database/baaa010 (Year: 2020), pp. 1-35.

Ruiz Ivan et al., "Towards a physical rehabilitation system using a telemedicine approach", Computer Methods in Biomechanics and Biomedical Engineering: Imaging & Visualization, vol. 8, No. 6, Jul. 28, 2020, pp. 671-680, XP055914810.

De Canniere Helene et al., "Wearable Monitoring and Interpretable Machine Learning Can Objectively Track Progression in Patients during Cardiac Rehabilitation", Sensors, vol. 20, No. 12, Jun. 26, 2020, XP055914617, pp. 1-15.

Boulanger Pierre et al., "A Low-cost Virtual Reality Bike for Remote Cardiac Rehabilitation", Dec. 7, 2017, Advances in Biometrics: International Conference, ICB 2007, Seoul, Korea, pp. 155-166.

Yin Chieh et al., "A Virtual Reality-Cycling Training System for Lower Limb Balance Improvement", BioMed Research International, vol. 2016, pp. 1-10.

Gerbild et al., "Physical Activity to Improve Erectile Dysfunction: A Systematic Review of Intervention Studies," Sexual Medicine, 2018, 15 pages.

Jeong et al., "Computer-assisted upper extremity training using interactive biking exercise (iBikE) platform," Sep. 2012, pp. 1-5, 34th Annual International Conference of the IEEE EMBS.

International Search Report and Written Opinion for PCT/US2023/014137, dated Jun. 9, 2023, 13 pages.

Website for "Esino 2022 Physical Therapy Equipments Arm Fitness Indoor Trainer Leg Spin Cycle Machine Exercise Bike for Elderly," https://www.made-in-china.com/showroom/esinogroup/product-detailYdZlwGhCMKVR/China-Esino-2022-Physical-Therapy-Equipments-Arm-Fitness-Indoor-Trainer-Leg-Spin-Cycle-Machine-Exercise-Bike-for-Elderly.html, retrieved on Aug. 29, 2023, 5 pages.

Abedtash, "An Interoperable Electronic Medical Record-Based Platform for Personalized Predictive Analytics", ProQuest LLC, Jul. 2017, 185 pages.

Claris Healthcare Inc., Claris Reflex Patient Rehabilitation System Brochure, retrieved on Oct. 2, 2019, 5 bages, https://clarisreflex.com/.

Fysiomed, 16983—Vario adjustable pedal arms, retrieved from timestamp of Jun. 7, 2017 from https://web.archive.org/web/20160607052632/https://www.fysiomed.com/en/products/16983-vario-adjustable-pedal-arms on Dec. 15, 2021, 4 pages.

HCL Fitness, HCI Fitness PhysioTrainer Upper Body Ergonometer, announced 2009 [online], retrieved on Aug. 19, 2021, 8 pages, www.amazon.com/HCI-Fitness-PhysioTrainer-Upper-Ergonometer/dp/B001P5GUGM.

HCL Fitness, HCI Fitness PhysioTrainer Pro, 2017, retrieved on Aug. 19, 2021, 7 pages, https://www.amazon.com/HCI-Fitness-Physio Trainer-Electronically-Controlled/dp/B0759YMW78/.

International Preliminary Report on Patentability of International Application No. PCT/US2017/50895, Date of Mailing Dec. 11, 2018, 52 pages.

(56) References Cited

OTHER PUBLICATIONS

International Searching Authority, Search Report and Written Opinion for International Application No. PCT/US2017/50895, Date of Mailing Jan. 12, 2018, 6 pages.
International Searching Authority, Search Report and Written Opinion for International Application No. PCT/US2020/021876, Date of Mailing May 28, 2020, 8 pages.
International Searching Authority, Search Report and Written Opinion for International Application No. PCT/US2020/051008, Date of Mailing Dec. 10, 2020, 9 pages.
International Searching Authority, Search Report and Written Opinion for International Application No. PCT/US2020/056661, Date of Mailing Feb. 12, 2021, 12 pages.
Matrix, R3xm Recumbent Cycle, retrieved on Aug. 4, 2020, 7 pages, https://www.matrixfitness.com/en/cardio/cycles/r3xm-recumbent.
ROM3 Rehab, ROM3 Rehab System, Apr. 20, 2015, retrieved on Aug. 31, 2018, 12 pages, https://vimeo.com/125438463.
International Searching Authority, Search Report and Written Opinion for International Application No. PCT/US2021/032807, Date of Mailing Sep. 6, 2021, 11 pages.
Jennifer Bresnick, "What is the Role of Natural Language Processing in Healthcare?", pp. 1-7, published Aug. 18, 2016, retrieved on Feb. 1, 2022 from https://healthitanalytics.com/ featu res/what-is-the-role-of-natural-language-processing-in-healthcare.
Alex Bellec, "Part-of-Speech tagging tutorial with the Keras Deep Learning library," pp. 1-16, published Mar. 27, 2018, retrieved on Feb. 1, 2022 from https://becominghuman.ai/part-of-speech-tagging-tutorial-with-the-keras-deep-learning-library-d7f93fa05537.
Kavita Ganesan, All you need to know about text preprocessing for NLP and Machine Learning, pp. 1-14, published Feb. 23, 2019, retrieved on Feb. 1, 2022 from https:// towardsdatascience.com/all-you-need-to-know-about-text-preprocessing-for-nlp-and-machine-learning-bcl c5765ff67.
Badreesh Shetty, "Natural Language Processing (NPL) for Machine Learning," pp. 1-13, published Nov. 24, 2018, retrieved on Feb. 1, 2022 from https://towardsdatascience. com/natural-language-processing-nlp-for-machine-learning-d44498845d5b.
Website for "Pedal Exerciser", p. 1, retrieved on Sep. 9, 2022 from https://www.vivehealth.com/collections/physical-therapy-equipment/products/pedalexerciser.
Website for "Functional Knee Brace with ROM", p. 1, retrieved on Sep. 9, 2022 from http://medicalbrace.gr/en/product/functional-knee-brace-with-goniometer-mbtelescopicknee/.
Website for "ComfySplints Goniometer Knee", pp. 1-5, retrieved on Sep. 9, 2022 from https://www.comfysplints.com/product/knee-splints/.
Website for "BMI FlexEze Knee Corrective Orthosis (KCO)", pp. 1-4, retrieved on Sep. 9, 2022 from https://orthobmi.com/products/bmi-flexeze%C2%AE-knee-corrective-orthosis-kco.
Website for "Neoprene Knee Brace with goniometer—Patella Rom MB.4070", pp. 1-4, retrieved on Sep. 9, 2022 from https://www.fortuna.com.gr/en/product/neoprene-knee-brace-with-goniometer-patella-rom-mb-4070/.
Kuiken et al., "Computerized Biofeedback Knee Goniometer: Acceptance and Effect on Exercise Behavior in Post-total Knee Arthroplasty Rehabilitation," Biomedical Engineering Faculty Research and Publications, 2004, pp. 1-10.
Ahmed et al., "Artificial intelligence with multi-functional machine learning platform development for better healthcare and precision medicine," Database, 2020, pp. 1-35.
Davenport et al., "The potential for artificial intelligence in healthcare," Digital Technology, Future Healthcare Journal, 2019, pp. 1-5, vol. 6, No. 2.
Website for "OxeFit XS1", pp. 1-3, retrieved on Sep. 9, 2022 from https://www.oxefit.com/xs1.
Website for "Preva Mobile", pp. 1-6, retrieved on Sep. 9, 2022 from https://www.precor.com/en-us/resources/introducing-preva-mobile.
Website for "J-Bike", pp. 1-3, retrieved on Sep. 9, 2022 from https://www.magneticdays.com/en/cycling-for-physical-rehabilitation.
Website for "Excy", pp. 1-12, retrieved on Sep. 9, 2022 from https://excy.com/portable-exercise-rehabilitation-excy-xcs-pro/.
Website for "OxeFit XP1", p. 1, retrieved on Sep. 9, 2022 from https://www.oxefit.com/xp1.
Jeong et al., "Remotely controlled biking is associated with improved adherence to prescribed cycling speed," Technology and Health Care 23, 2015, 7 pages.
Laustsen et al., "Telemonitored exercise-based cardiac rehabilitation improves physical capacity and health-related quality of life," Journal of Telemedicine and Telecare, 2020, DOI: 10.1177/1357633X18792808, 9 pages.
Blasiak et al., "CURATE.AI: Optimizing Personalized Medicine with Artificial Intelligence,"SLAS TECHNOLOGY: Translating Life Sciences Innovation, 2020, 11 pages.
Ahmed et al., "Artificial Intelligence With Multi-Functional Machine Learning Platform Development for Better Healthcare and Precision Medicine," Database (Oxford), 2020, pp. 1-35, vol. 2020.
Davenport et al., "The Potential for Artificial Intelligence in Healthcare," Future Healthcare Journal, 2019, pp. 94-98, vol. 6, No. 2.

\* cited by examiner

SYSTEM AND METHOD FOR TRANSMITTING DATA AND ORDERING ASYNCHRONOUS DATA

CROSS-REFERENCES TO RELATED APPLICATIONS

This application is continuation of U.S. patent application Ser. No. 17/149,457, filed Jan. 14, 2021, titled "System and Method for Transmitting Data and Ordering Asynchronous Data", which is a continuation-in-part of U.S. patent application Ser. No. 17/021,895, filed Sep. 15, 2020, titled "Telemedicine for Orthopedic Treatment," which claims priority to and the benefit of U.S. Provisional Patent Application Ser. No. 62/910,232, filed Oct. 3, 2019, titled "Telemedicine for Orthopedic Treatment," the entire disclosures of which are hereby incorporated by reference for all purposes. As a continuation of U.S. patent application Ser. No. 17/149,457, this application also claims priority to and the benefit of U.S. Provisional Patent application Ser. No. 63/028,399, filed May 21, 2020, titled "System and Method for Transmitting Data and Ordering Asynchronous Data," the entire disclosures of which are hereby incorporated by reference for all purposes.

TECHNICAL FIELD

This disclosure relates generally to systems and methods of transmitting and processing data.

BACKGROUND

Medical devices may include one or more sensors that detect events and generate data pertaining to the events. The data from the sensors may flow in a data stream from the device to a network and, optionally, back to the device. This process can generate exceedingly large amounts of data, requiring substantial memory to use and to store the data. The data may be input into an electronic medical record (EMR) system. EMRs can include information related to the health of a patient, and such information may be contained in or called an "electronic health record." The EMR can use and store electronic health records of patients (e.g., a collection of patient and population health information in a digital format). The health information may be used by a variety of entities, such as health care providers (e.g., physicians, physical therapists, nurses, etc.); insurance companies; billing companies; hospitals; laboratory service providers; psychological service providers (e.g., psychiatrists, psychologists, counselors, social workers); or any other suitable entity. These entities may use the health information to enable the determination of optimal treatments for their patients, to provide or deliver those treatments; and to accurately bill for the associated healthcare services provided to the patients. However, the substantial amount of memory that may be required to use and to store the data generated by the medical devices may result in higher healthcare costs. Further, bulk transmission of data from the medical devices to remote servers may impact network performance by causing higher peak network loads. In addition, waiting for data collection to complete before processing data may prevent health care providers from acting on error information or detecting problems with medical devices as quickly as possible. The use of telemedicine may increase the number of medical devices used by patients in their homes. For example, healthcare professionals may lease the medical devices to patients to use for rehabilitating from an injury or a surgery. A reduction in memory needed for medical devices to properly function may reduce the cost of the medical device and the fees for leasing the medical devices, resulting in reduced healthcare expenses. Further, as bulk transmission of large data files from medical devices may result in higher peak network loads, it may be desirable to reduce the size of individual files being transmitted. Further, transmitting data closer to the time it is generated may enable easier access to error information and faster responses to medical devices on which problems have been detected.

SUMMARY

In general, the present disclosure provides systems and methods for transmitting data and ordering asynchronous data.

In one aspect, a computer-implemented system includes an electromechanical device configured to be manipulated by a patient while performing an exercise session, and a processor in communication with the electromechanical device. The processor is configured to receive data, generate a map packet, and transmit the map packet. The processor is configured to use the data to generate continuity packets, where each of the continuity packets includes a contiguous portion of the data, and transmit the continuity packets. The processor is configured to use the map packet and the continuity packets to cause an output file to be generated.

In one aspect, a system for transmitting data is disclosed. The system includes an information-generating device and a processor in communication with the information-generating device. The processor is configured to receive data; to generate a map packet; to transmit the map packet; using the data, to generate continuity packets, wherein each of the continuity packets comprises a contiguous portion of the data; to transmit the continuity packets; and using the map packet and the continuity packets, to cause an output file to be generated.

In another aspect, a method for operating an information-generating device is disclosed. The method includes receiving data; generating a map packet; transmitting the map packet; using the data to generate continuity packets, wherein each of the continuity packets comprises a contiguous portion of the data; transmitting the continuity packets; and using the map packet and the continuity packets to cause an output file to be generated.

In yet another aspect, a tangible, non-transitory computer-readable storage medium is disclosed. The tangible, non-transitory computer-readable storage medium stores instructions that, when executed, cause a processor to receive data from an information-generating device; to generate a map packet; to transmit the map packet; using the data, to generate continuity packets, wherein each of the continuity packets comprises a contiguous portion of the data; to transmit the continuity packets; and using the map packet and the continuity packets, to cause an output file to be generated.

In yet another aspect, a system for ordering of asynchronously transmitted data is disclosed. The system includes a processor configured to receive, from an information-generating device, a map packet and continuity packets in an initial order. Responsive to receiving the map packet and at least two of the continuity packets, the processor is configured to use the map packet to generate an output file by ordering the continuity packets from the initial order into an output order.

In yet another aspect, a method for operating a computing device is disclosed. The method includes receiving, from an information-generating device, a map packet and continuity packets in an initial order, and, responsive to receiving the map packet and at least two of the continuity packets, using the map packet to generate an output file by ordering the continuity packets from the initial order into an output order.

In yet another aspect, a tangible, non-transitory computer-readable storage medium is disclosed. The tangible, non-transitory computer-readable storage medium stores instructions that, when executed, cause a processor to receive, from an information-generating device, a map packet and continuity packets in an initial order. Responsive to receiving the map packet and at least two of the continuity packets, the instructions cause the processor to use the map packet to generate an output file by ordering the continuity packets from the initial order into an output order.

In yet another aspect, a system for transmission and ordering of asynchronous data is disclosed. The system comprises an information-generating device comprising a device-side processor. The device-side processor is configured to receive data; generate a map packet; transmit the map packet; use the data to generate continuity packets, wherein each of the continuity packets comprises a contiguous portion of the data; and transmit the continuity packets. The system further comprises a remote computing device comprising a remote processor. The remote processor is configured to receive, from the information-generating device, the map packet; to receive, from the information-generating device, the continuity packets in an initial order; and responsive to receiving at least two of the continuity packets and the map packet, to use the map packet to generate an output file by ordering the continuity packets from the initial order into an output order.

Other technical features may be readily apparent to one skilled in the art from the following figures, descriptions, and claims.

Before undertaking the DETAILED DESCRIPTION below, it may be advantageous to set forth definitions of certain words and phrases used throughout this patent document. The term "couple" and its derivatives refer to any direct or indirect communication between two or more elements, independent of whether those elements are in physical contact with one another. The terms "transmit," "receive," and "communicate," as well as derivatives thereof, encompass both direct and indirect communication. The terms "transmit," "receive," and "communicate," as well as derivatives thereof, encompass both communication with remote systems and communication within a system, including reading and writing to different portions of a memory device. The terms "include" and "comprise," as well as derivatives thereof, mean inclusion without limitation. The term "or" is inclusive, meaning and/or. The phrase "associated with," as well as derivatives thereof, means to include, be included within, interconnect with, contain, be contained within, connect to or with, couple to or with, be communicable with, cooperate with, interleave, juxtapose, be proximate to, be bound to or with, have, have a property of, have a relationship to or with, or the like. The term "controller" means any device, system or part thereof that controls at least one operation. Such a controller may be implemented in hardware or a combination of hardware and software and/or firmware. The functionality associated with any particular controller may be centralized or distributed, whether locally or remotely. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

Moreover, various functions described below can be implemented or supported by one or more computer programs, each of which is formed from computer readable program code and embodied in a computer readable storage medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable storage medium" includes any type of medium capable of being accessed by a computer, such as read only memory (ROM), random access memory (RAM), a hard disk drive, a flash drive, a compact disc (CD), a digital video disc (DVD), solid state drive (SSD), or any other type of memory. A "non-transitory" computer readable storage medium excludes wired, wireless, optical, or other communication links that transport transitory electrical or other signals. A non-transitory computer-readable storage medium includes media where data can be permanently stored and media where data can be stored and later overwritten, such as a rewritable optical disc or an erasable memory device.

Definitions for other certain words and phrases are provided throughout this patent document. Those of ordinary skill in the art should understand that in many if not most instances, such definitions apply to prior as well as future uses of such defined words and phrases.

BRIEF DESCRIPTION OF THE DRAWINGS

For a more complete understanding of this disclosure and its advantages, reference is now made to the following description, taken in conjunction with the accompanying drawings. It is emphasized that, according to common practice, the various features of the drawings are not to-scale. On the contrary, the dimensions of the various features are arbitrarily expanded or reduced for clarity.

DETAILED DESCRIPTION

FIGS. 1-5, discussed below, and the various embodiments used to describe the principles of this disclosure are by way of illustration only and should not be construed in any way to limit the scope of the disclosure.

Figure 1:
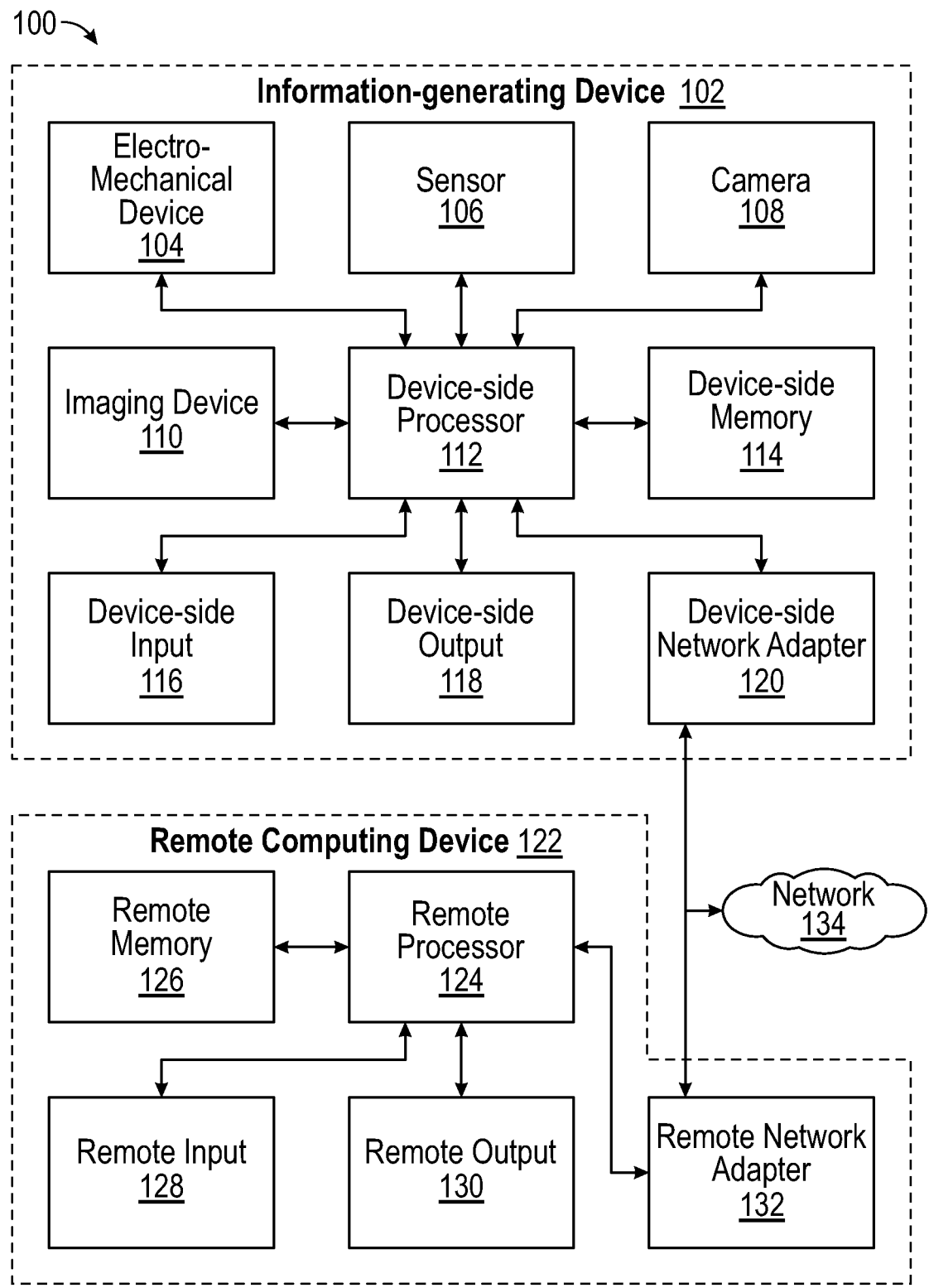
FIG. 1 illustrates a component diagram of an illustrative system for transmitting and ordering asynchronous data according to certain aspects of this disclosure.

FIG. 1 illustrates a component diagram of an illustrative system 100 for transmitting and ordering asynchronous data in accordance with aspects of this disclosure. The system 100 may include an information-generating device 102. The information-generating device 102 may be a medical device.

Figure 2:
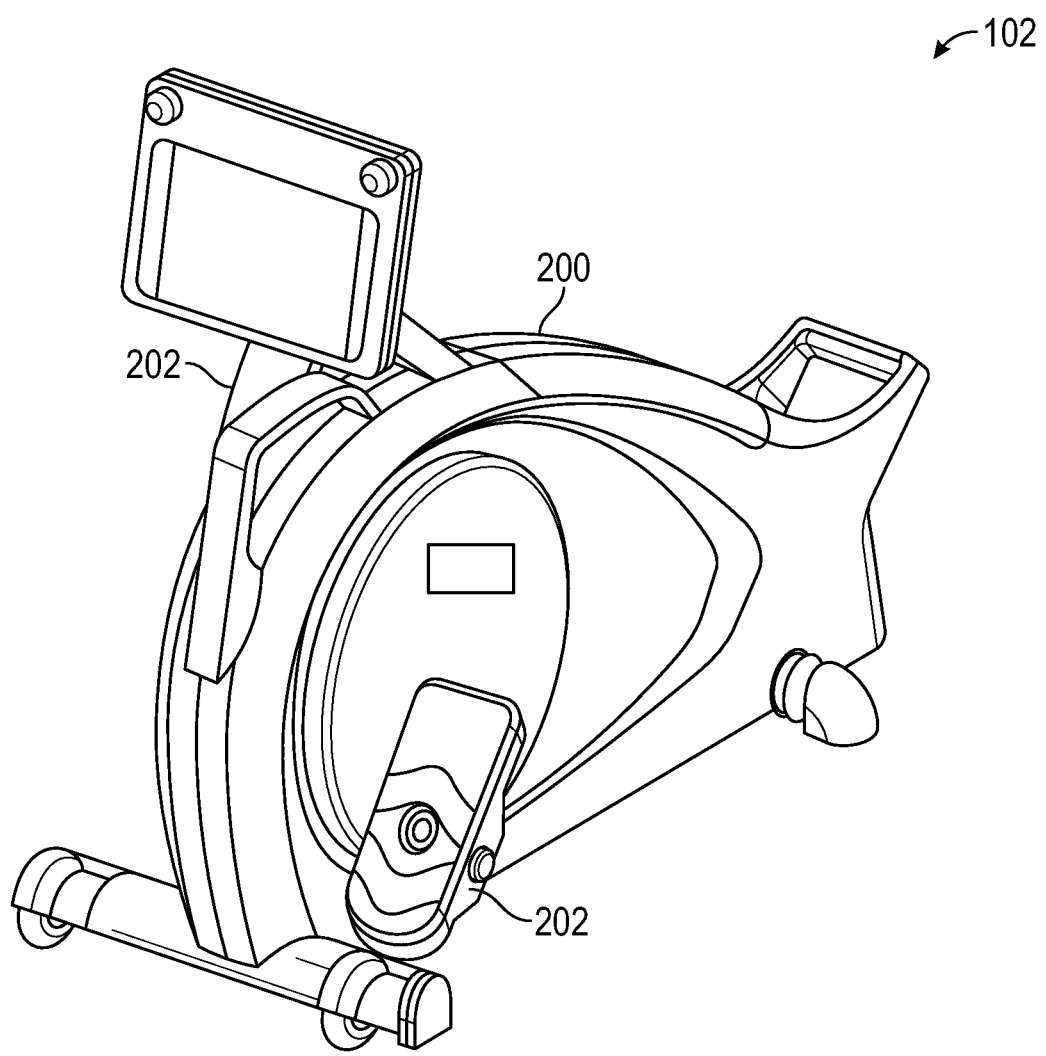
FIG. 2 illustrates an example information-generating device according to certain aspects of this disclosure.

The medical device may be a testing device, a diagnostic device, a therapeutic device, or any other suitable medical device. "Medical device" as used in this context may refer to hardware, software, or a mechanical or other device that may assist in a medical service, regardless of whether it is FDA (or other governmental regulatory body of any given country) approved, required to be FDA (or other governmental regulatory body of any given country) approved or available commercially or to consumers without such approval. Non-limiting examples of the medical devices include an insulin pump, a thermometer, an MRI machine, a CT-scan machine, a glucose meter, an apheresis machine, and a physical therapy machine (e.g., an orthopedic rehabilitation device, such as a physical therapy cycle). Non-limiting examples of places where the medical device may be located include a healthcare clinic, a physical rehabilitation center, and a user's home to allow for telemedicine treatment, rehabilitation, and/or testing. FIG. 2 illustrates an example of the information-generating device 102 in which the information-generating device 102 is a physical therapy cycle 200.

The information-generating device 102 may include an electromechanical device 104, such as pedals 202 of the physical therapy cycle 200, a goniometer configured to attach to a joint and measure joint angles, or any other suitable electromechanical device. The electromechanical device 104 may be configured to be manipulated by a patient while performing an exercise session. The electromechanical device 104 may be configured to transmit information, such as pedal position information. A non-limiting example of positioning information includes information relating to the location of the electromechanical device 104 (e.g., the pedals 202).

The information-generating device 102 may include a sensor 106. The sensor 106 can be used for obtaining information, such as fingerprint information, retina information, voice information, height information, weight information, vital sign information (e.g., blood pressure, heart rate, etc.), response information to physical stimuli (e.g., change in heart rate while running on a treadmill), performance information (rate of speed of rotation of the pedals 202 of the physical therapy cycle 200), or any other suitable information. The sensor 106 may be a temperature sensor (such as a thermometer or thermocouple), a strain gauge, a proximity sensor, an accelerometer, an inclinometer, an infrared sensor, a pressure sensor, a light sensor, a smoke sensor, a chemical sensor, any other suitable sensor, a fingerprint scanner, a sound sensor, a microphone, or any combination thereof. The sensor 106 may be located on an interior or exterior of the device. For example, the sensor 106 may be a pedal position sensor located on the pedals 202 of the physical therapy cycle 200.

The information-generating device 102 may include a camera 108, such as a still image camera, a video camera, an infrared camera, an X-ray camera, any other suitable camera, or any combination thereof. The information-generating device 102 may include an imaging device 110, such as an MRI imaging device, an X-ray imaging device, a thermal imaging device, any other suitable imaging device, or any combination thereof. The information-generating device 102 may include a device-side processor 112. The device-side processor 112 can include, for example, computers, intellectual property (IP) cores, application-specific integrated circuits (ASICs), programmable logic arrays, optical processors, programmable logic controllers, microcode, microcontrollers, servers, microprocessors, digital signal processors, any other suitable circuit, or any combination thereof.

The device-side processor may be in communication with the electromechanical device 104, the sensor 106, the camera 108, the imaging device 110, any other suitable device, or any combination thereof.

The information-generating device 102 may include a device-side memory 114 in communication with the device-side processor 112. The device-side memory 114 can include any type of memory capable of being accessed by a computer, such as read only memory (ROM), random access memory (RAM), a hard disk drive, a flash drive, a compact disc (CD), a digital video disc (DVD), solid state drive (SSD), or any other suitable type of memory. The device-side memory 114 may store instructions that cause the device-side processor 112 to perform a series of actions or processes.

The information-generating device 102 may include a device-side input 116 in communication with the device-side processor 112. Examples of the device-side input 116 include a keyboard, a keypad, a mouse, a microphone supported by speech-to-text software, or any other suitable input device. The device-side input 116 may be used by a medical system operator to input information, such as user-identifying information, observational notes, or any other suitable information. An operator is to be understood throughout this disclosure to include people, bots, robots, hardware, and/or computer software, such as programs or artificial intelligence, and any combination thereof.

The information-generating device 102 may include a device-side output 118 in communication with the device-side processor 112. The device-side output 118 may be used to provide information to the operator or a user (or patient) of the information-generating device 102. For the purposes of this disclosure, user and patient are used interchangeably. Examples of the device-side output 118 may include a display screen, a speaker, an alarm system, or any other suitable output device, including haptic, tactile, olfactory, or gustatory ones. In some embodiments, such as where the information-generating device 102 includes a touchscreen, the device-side input 116 and the device-side output 118 may be the same device.

For communicating with remote computers and servers, the information-generating device 102 may include a device-side network adapter 120 in communication with the device-side processor 112. The device-side network adapter 120 may include wired or wireless network adapter devices (e.g., a wireless modem or Bluetooth) or a wired network port.

The information-generating device 102 may be coupled to or be in communication with a remote computing device 122. The remote computing device 122 may include a remote processor 124. The remote processor 124 can include, for example, computers, intellectual property (IP) cores, application-specific integrated circuits (ASICs), programmable logic arrays, optical processors, programmable logic controllers, microcode, microcontrollers, servers, microprocessors, digital signal processors, any other suitable circuit, or any combination thereof The remote computing device 122 may include a remote memory 126 in communication with the remote processor 124. The remote memory 126 can include any type of memory capable of being accessed by a computer, such as read only memory (ROM), random access memory (RAM), a hard disk drive, a flash drive, a compact disc (CD), a digital video disc (DVD), solid state drive (SSD), or any other suitable type of memory. The remote memory 126 may store instructions that cause the remote processor 124 to perform a series of actions or processes.

The remote computing device 122 may include a remote input 128 in communication with the remote processor 124. Examples of the remote input 128 include a keyboard, a keypad, a mouse, a microphone supported by speech-to-text software, or any other suitable input device. The remote input 128 may be used by a medical system operator to input information, such as user-identifying information, observational notes, or any other suitable information. An operator is to be understood throughout this disclosure to include people, bots, robots, hardware, and/or computer software, such as programs or artificial intelligence, and any combination thereof.

The remote computing device 122 may include a remote output 130 in communication with the remote processor 124. The remote output 130 may be used to provide information to the operator or a user (or patient) of the remote computing device 122. For the purposes of this disclosure, user and patient are used interchangeably. Examples of the remote output 130 may include a display screen, a speaker, an alarm system, or any other suitable output device, including haptic, tactile, olfactory, or gustatory ones. In some embodiments, such as where the remote computing device 122 includes a touchscreen, the remote input 128 and the remote output 130 may be the same device.

For communicating with the information-generating device 102, as well as remote computers and servers, the remote computing device 122 may include a remote network adapter 132 in communication with the remote processor 124. The remote network adapter 122 may include wired or wireless network adapter devices (e.g., a wireless modem or Bluetooth) or a wired network port.

Both the device-side network adapter 120 and the remote network adapter 132 may be in communication with a network 134. Transmissions between the information-generating device 102 and the remote computing device 122 may pass through the network 134. The network 134 may be a public network (e.g., connected to the Internet via wired (Ethernet) or wireless (Wi-Fi)), a private network (e.g., a local area network (LAN) or wide area network (WAN)), a combination thereof, or any other suitable network.

Any time information is transmitted or communicated, the information may be in EDI file format or any other suitable file format. In any of the processes or steps of the method, file format conversions may take place. By utilizing Internet of Things (IoT) devices or gateways, data streams, ETL bucketing, EDI mastering, or any other suitable technique, data can be mapped, converted, translated, or transformed into a carrier-preferred state. As a result of the volume of data being transmitted, the data security requirements, and the data consistency requirements, an enterprise grade architecture may be utilized for reliable data transfer.

FIG. 1 is not intended to be limiting: the system 100, the information-generating device 102, and the remote computing device 122 may include more or fewer components than those illustrated in FIG. 1.

Figure 3A:
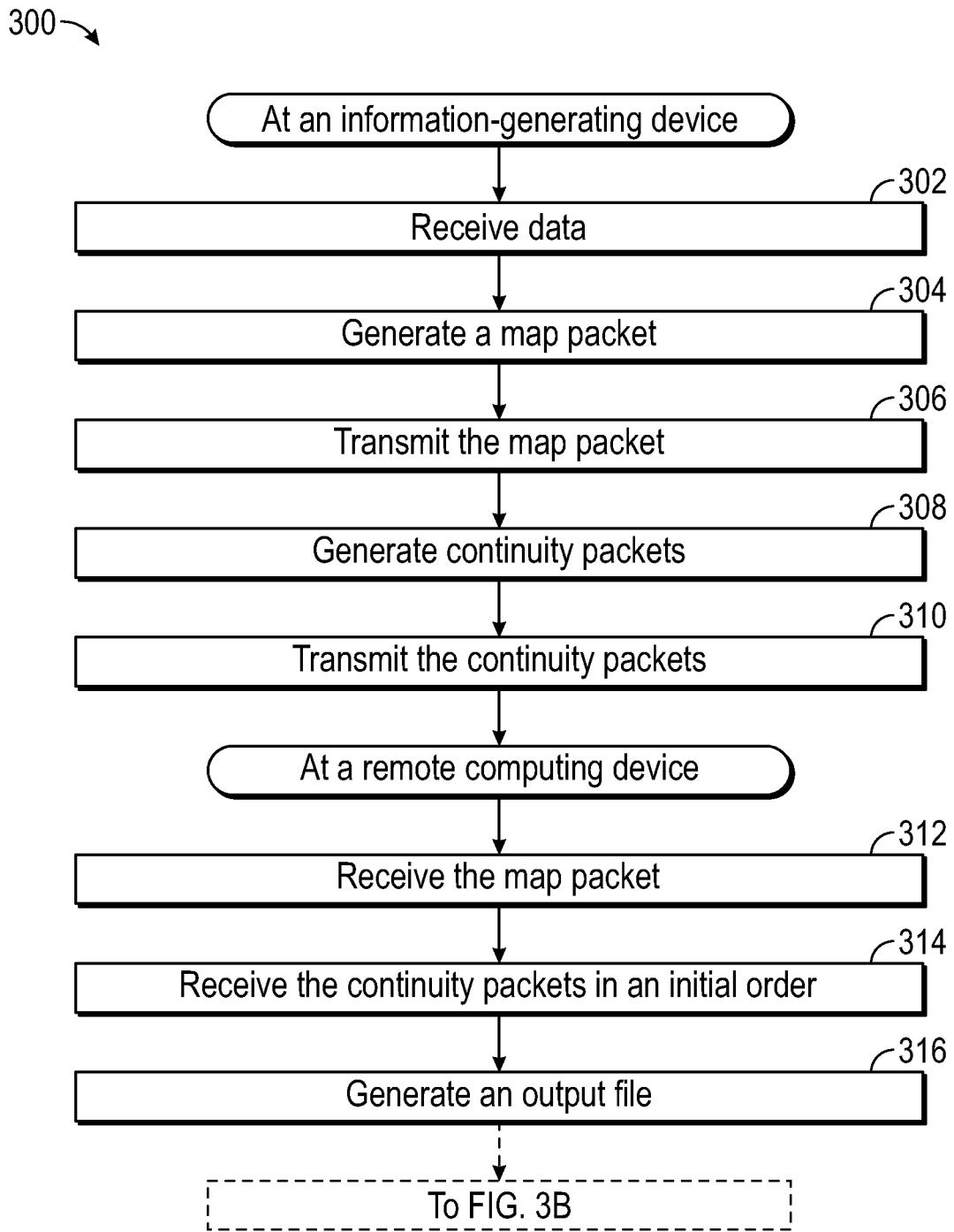
FIGS. 3A and 3B illustrate a method for transmitting data and ordering asynchronous data according to certain aspects of this disclosure.
Figure 3B:
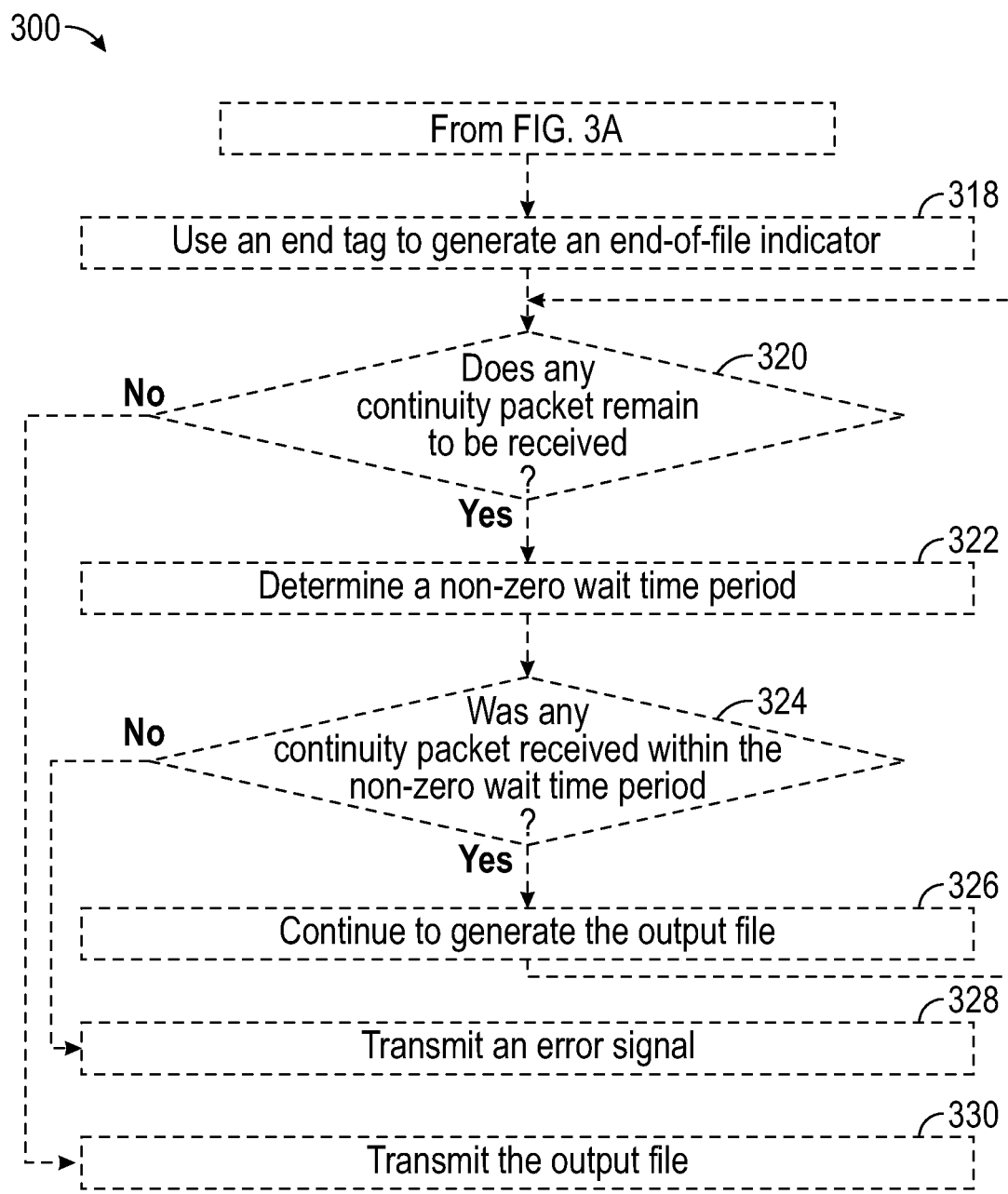

FIGS. 3A and 3B illustrate a computer-implemented method 300 for transmitting data and ordering asynchronous data. The method 300 may be performed by the system 100 using the information-generating device 102 and the remote computing device 122. The method 300 may be implemented on a pair of processors, such as the device-side processor 112 and the remote processor 124, which are together configured to perform the steps of the method 300. The method 300 may include operations implemented in instructions stored on one or more memory devices, such as the device-side memory 114 and the remote memory 126, and be executed by one or more processors, such as the device-side processor 112 and the remote processor 124. The steps of the method 300 may be stored in one or more non-transient computer-readable storage media.

At step 302, the method 300 includes, at the information-generating device 102, receiving data. For example, the device-side processor 112 can receive data from the electromechanical device 104, the sensor 106, the camera, 108, the imaging device 110, the device-side input 116, or any other suitable device. As a more specific example, the device-side processor 112 may receive an MII image from an MII imaging device (i.e., the imaging device 110). The data may be received as a stream of data. The stream of data may be a continuous stream of data. The device-side processor 112 may initially receive the data as a digital signal, an analog signal, or any other suitable signal. The device-side processor 112 may convert data from an analog signal to a digital signal.

At step 304, the method 300 includes, at the information-generating device, generating a map packet. The map packet contains data mapping information that indicates a means, a method, an approach or another mechanism for receiving the continuity packets. In some embodiments, the map packet includes end-of-file information that function as information against which data from later-received continuity packets can be compared for determining whether data transmission for a given file has ended. For example, the map packet may contain data mapping information indicating that the continuity packets will have a header following the format of "AA######AA", and an end-of-file continuity packet will have an end-of-file header following the format of "AA######ZZ". In this example, "######" indicates a numerical value starting at "000000" and going to a possible maximum of "999999" and "ZZ" functions as an end tag to indicate that the tagged continuity packet is the final continuity packet of the given file.

At step 306, the method 300 includes, at the information-generating device, transmitting the map packet. For example, the device-side processor 112 may direct the device-side network adapter 120 to transmit the map packet to the remote network adapter 132 of the remote computing device 122.

At step 308, the method 300 includes, at the information-generating device, generating the continuity packets. Each of the continuity packets is a data packet that includes a contiguous portion of the data. The continuity packets may be generated using the data. For example, the device-side processor 112 may take a contiguous portion of the data and place that contiguous portion into one of the continuity packets. One or more of the continuity packets may include header information that the processor can use to order the continuity packets. For example, a first continuity packet may include a first header including first header information of "AA000000AA", and a second continuity packet may include a second header including second header information of "AA000001AA". A contiguous portion of the data mapping information of the map packet may correspond to a contiguous portion of the header information. For example, the header information may include a contiguous portion of data, including the string "AA". The string "AA" corresponds with a portion of the mapping information of the map packet, thereby indicating that header information of relevant continuity packets will contain the string "AA". The header information may also include information pertaining to the portion of data contained in the continuity packet. The information-generating device generates the continuity packets in an initial order; however, a remote computing device 122 may not receive the continuity packets in the initial order (e.g., a first continuity packet may be generated first and a second continuity packet may be generated second, but the second packet may be received before the first packet is received). Thus, the header information may include information that the remote computing device 122 can use to order (e.g., reassemble) the continuity packets, such as the initial order that the continuity packets were generated. The header information of an end-of-file continuity packet can include an end tag corresponding to a contiguous portion of the end-of-file information. For example, an end-of-file continuity packet may include end-of-file header information of "AA000002ZZ", where "ZZ" functions as the end tag. The generation of the continuity packets may occur all at once or be spread out over time as more data is received, so the end-of file header information is used to indicate an end of the data stream.

At step 310, the method 300 includes, at the information-generating device, transmitting the continuity packets. For example, the device-side processor 112 may direct the device-side network adapter 120 to transmit the continuity packets to the remote network adapter 132 of the remote computing device 122. This transmission may occur after all continuity packets have been generated, as the continuity packets are being generated, or any combination thereof. In cases where the generation of the continuity packets is spread out over time as more data is received, the generation and the transmission of the continuity packets allow for a reduced memory requirement and reduced peak network loads relative to first waiting for all of the data to be received. For instance, if, before generating the continuity packets, the information-generating device waits until all of the data is received (e.g., from the sensors), the device-side memory 114 may have to store the entirety of the data (i.e., which may require a substantial amount of memory to store an extremely large file), rather than temporarily storing a portion of the data while the device-side processor 112 generates and transmits each continuity packet. Similarly, if, before transmitting the continuity packets, the information-generating device waits until all of the data has been received and all of the continuity packets have been generated, the network loads required for the transmission may be higher because a larger amount of data is being transmitted at once (e.g., all of the continuity packets are being transmitted in a short time period).

At step 312, the method 300 includes, at the remote computing device (e.g., the remote computing device 122), receiving the map packet. The map packet may be received from the information-generating device 102. For example, the remote computing device 122 may receive the map packet by way of the remote network adapter 132.

At step 314, the method 300 includes, at the remote computing device, receiving continuity packets in an initial order. The continuity packets may be received from the information-generating device 102. For example, continuity packets may be received by the remote computing device 122 by way of the remote network adapter 132 in an initial order wherein the second continuity packet is received first, the first continuity packet is received second, and the end-of-file continuity packet is received third.

At step 316, the method 300 includes, at the remote computing device, generating an output file. Responsive to receiving at least two of the continuity packets and the map packet, the map packet may be used to generate an output file. The output file may be generated by ordering the continuity packets from the initial order into an output order. For example, given the initial order described above in step 314, the remote processor 124 may order the continuity packets, or contiguous portions of the continuity packets corresponding to contiguous portions of the data, into an output order. The output order may be as follows: 1) the first continuity packet, 2) the second continuity packet, and 3) the end-of-file continuity packet. In some embodiments, as the remote processor receives the continuity packets, the remote processor may contemporaneously generate the output file. For example, the remote computing device 124 may receive the second continuity packet first and the first continuity packet second, but not yet have received the end-of-file continuity packet, in which case the remote processor 124 may order the continuity packets into an output order having the first continuity packet first and the second continuity packet second. In some embodiments, while the output file is being generated, the continuity packets are configured to be readable by external processes. Examples of such external processes include maintenance processes configured to check for device maintenance status or error messages. Such external processes may be able to read and/or respond to maintenance requests or errors prior to ordering, such that an error message contained in the continuity packets can be read prior to completing the generation of the output file. For example, if a patient is undergoing a CT scan performed by a CT scanner, a processor may monitor and read the data in real-time or near real-time to detect an error message. In this example, if the CT scanner generates a continuity packet containing an error message indicating a fault with the CT scanner (e.g., the data obtained by the CT scanner will be unusable), then, at the direction of such an external monitoring process, the remote processor 124 may read the error message prior to ordering and generating the output file and stop the CT scanner during the CT scan. Stopping the CT scan prior to its completion would limit the patient's unnecessary exposure to X-rays, as any exposure after the error may not result in usable data.

At step 318, the method 300 may include, at the remote computing device, using the end tag to generate an end-of-file indicator. For example, a flag may be used or a variable may be set as an end-of-file indicator when the end-of-file continuity packet containing the end tag "ZZ" is received (i.e., the remote processor may change a variable "end-of-file-reached" from "false" to "true").

At step 320, the method 300 may include using the header information, the map packet, and the end-of-file indicator to determine whether any continuity packets remain to be received. For example, if the first continuity packet containing the first header information of "AA000000AA" and the end-of-file continuity packet containing the end-of-file header information "AA000002ZZ" (and thus the end tag "ZZ") have been received, the remote processor 124 may determine that the second continuity packet has not been received. If any continuity packets remain to be received, the method 300 proceeds to step 322. If all continuity packets have been received, the method 300 proceeds to step 330.

At step 322, if any continuity packets remain to be received, the method 300 may include determining a non-zero wait time period. For example, if the second continuity packet has not been received, the remote processor 124 may determine a wait time period. The wait time period may be between two seconds and ten seconds, or any other suitable period of time.

At step 324, the method 300 may include, at the remote computing device, determining if any continuity packets were received within the wait time period. For example, if the second continuity packet, which had not been previously received, is received within the wait time period, the remote computing device may determine that a continuity packet was received within the wait time period, subsequent to which the method 300 proceeds to step 326. However, if the second continuity packet is not received within the wait time period, the remote processor 124 may determine that the continuity packet was not received within the wait time period, subsequent to which the method 300 proceeds to step 328.

At step 326, responsive to receiving another continuity packet within the non-zero wait time period, the method 300 may include the remote computing device continuing to generate the output file. For example, if the determination is that the second continuity packet that had not been previously received is received within the wait time period, then the remote processor 124 may continue generating the output file. The method 300 may return to step 320.

At step 328, responsive to determining the non-zero wait time period and not receiving another continuity packet within the non-zero wait time period, the method 300 may include the remote computing device transmitting an error signal. For example, if the determination is that the second continuity packet that had not been previously received was not received within the wait time period, the remote processor 124 may direct the remote network adapter 132 to transmit an error message and/or the remote output 130 to present the error message (e.g., "Error: Incomplete Data").

At step 330, responsive to determining that every continuity packet has been received, the method 300 includes transmitting the output file. For example, if the first continuity packet, the second continuity packet, and the end-of-file continuity packet have been received and ordered (e.g., into an output file), the remote processor 124 may direct the remote network adapter 132 to transmit the output file via the network 134.

Figure 4:
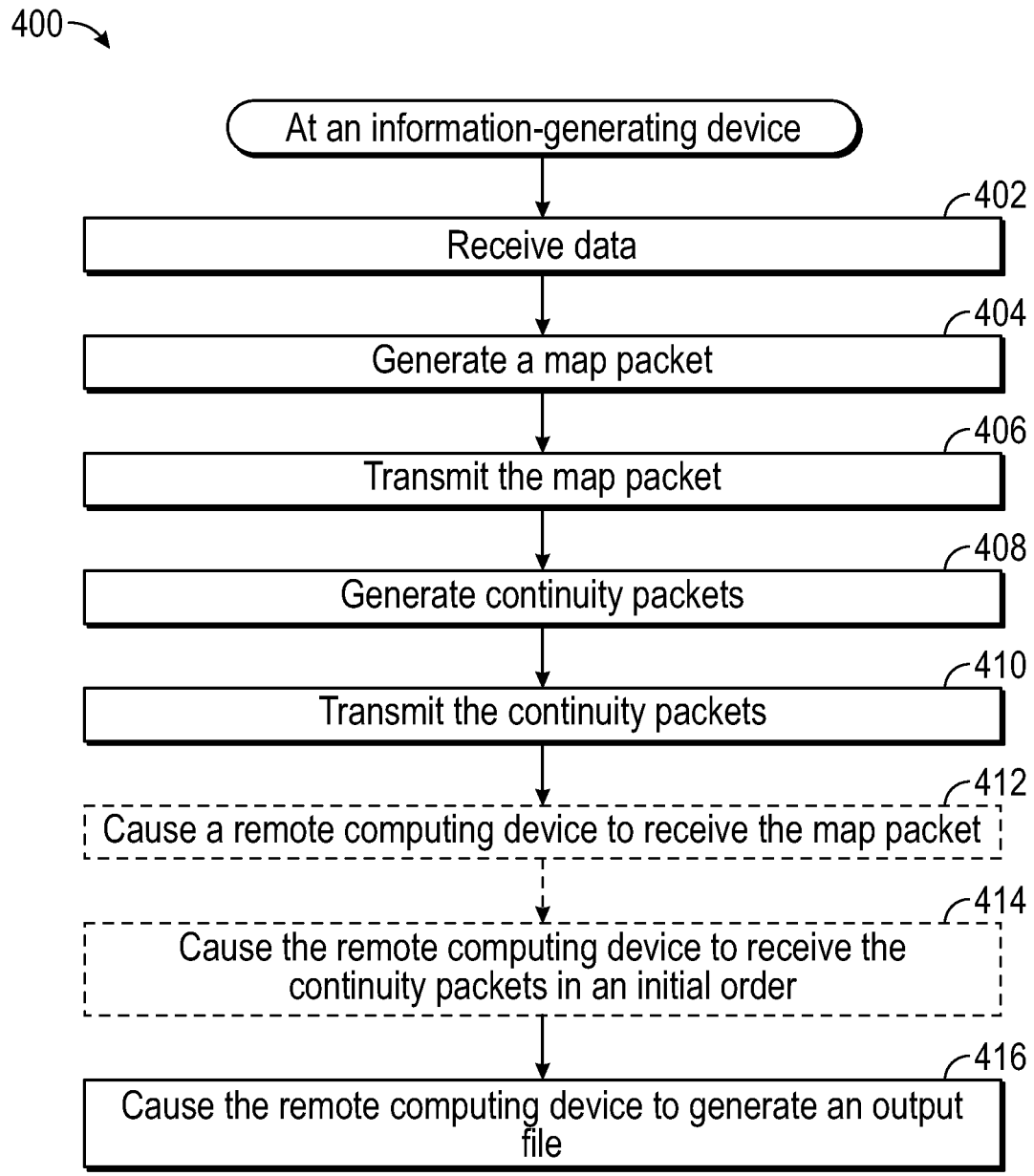
FIG. 4 illustrate a method for transmitting data according to certain aspects of this disclosure.

FIG. 4 illustrates a computer-implemented method 400 for transmitting data. Using the information-generating device 102, the method 400 may be performed by the system 100. The method 400 may be implemented on a processor, such as the device-side processor 112 configured to perform the steps of the method 400. The method 400 may include operations implemented in instructions stored on a memory device, such as the device-side memory 114 executed by a processor, such as the device-side processor 112. The steps of the method 300 may be stored on a non-transient computer-readable storage medium.

At step 402, the method 400 includes, at the information-generating device (e.g., the information-generating device 102), receiving data. For example, the device-side processor 112 can receive data from the electromechanical device 104, the sensor 106, the camera 108, the imaging device 110, the device-side input 116, or any other suitable device. As a more specific example, the device-side processor 112 may receive an MM image from an Mill imaging device (i.e., the imaging device 110). The data may be received as a stream of data. The stream of data may be a continuous stream of data. The device-side processor 112 may initially receive the data as a digital signal, an analog signal, or any other suitable signal. The device-side processor 112 may convert data from an analog signal to a digital signal.

At step 404, the method 400 includes, at the information-generating device, generating a map packet. The map packet contains data mapping information that indicates a means, a method, an approach, or another mechanism for receiving the continuity packets. In some embodiments, the map packet includes end-of-file information that function as information against which data from later-received continuity packets can be compared for determining whether data transmission for a given file has ended. For example, the map packet may contain data mapping information indicating that the continuity packets will have a header following the format of "AA######AA", and an end-of-file continuity packet will have an end-of-file header following the format of "AA######ZZ". In this example, "######" indicates a numerical value starting at "000000" and going to a possible maximum of "999999" and "ZZ" functions as an end tag to indicate that the tagged continuity packet is the final continuity packet of the given file.

At step 406, the method 400 includes, at the information-generating device, transmitting the map packet. For example, the device-side processor 112 may direct the device-side network adapter 120 to transmit the map packet to the remote network adapter 132 of the remote computing device 122.

At step 408, the method 400 includes, at the information-generating device, generating the continuity packets. Each of the continuity packets is a data packet that includes a contiguous portion of the data. The continuity packets may be generated using the data. For example, the device-side processor 112 may take a contiguous portion of the data and place that contiguous portion into one of the continuity packets. One or more of the continuity packets may include header information that the processor can use to order the continuity packets. For example, a first continuity packet may include a first header including first header information of "AA000000AA", and a second continuity packet may include a second header including second header information of "AA000001AA". A contiguous portion of the data mapping information of the map packet may correspond to a contiguous portion of the header information. For example, the header information may include a contiguous portion of data including the string "AA". The string "AA" corresponds to a portion of the mapping information of the map packet, indicating that header information of relevant continuity packets will contain the string "AA". The header information may also include information pertaining to the portion of data contained in the continuity packet. The information-generating device generates the continuity packets in an initial order; however, a remote computing device 122 may not receive the continuity packets in the initial order (e.g., a first continuity packet may be generated first and a second continuity packet may be generated second, but the second packet may be received before the first packet has been received). Thus, the header information may include information that the remote computing device 122 can use to order (e.g., reassemble) the continuity packets, such as the initial order that the continuity packets were generated. The header information of an end-of-file continuity packet can include an end tag corresponding to a contiguous portion of the end-of-file information. For example, an end-of-file continuity packet may include end-of-file header information of "AA000002ZZ", where "ZZ" functions as the end tag. The generation of the continuity packets may occur all at once or be spread out over time as more data is received, so the end-of file header information may be used to indicate an end of the data stream.

At step 410, the method 400 includes, at the information-generating device, transmitting the continuity packets. For example, the device-side processor 112 may direct the device-side network adapter 120 to transmit the continuity packets to the remote network adapter 132 of the remote computing device 122. This transmission may occur after all continuity packets have been generated, as the continuity packets are being generated, or any combination thereof. In cases where the generation of the continuity packets is spread out over time as more data is received, the generation and the transmission of the continuity packets allow for a reduced memory requirement and reduced peak network loads relative to waiting for all of the data to be received. For instance, if, before generating the continuity packets, the information-generating device waits until all of the data is received (e.g., from the sensors), the device-side memory 114 may have to store the entirety of the data (i.e., which may require a substantial amount of memory to store an exceedingly large file), rather than temporarily storing a portion of the data while the device-side processor 112 generates and transmits each continuity packet. Similarly, if, before transmitting the continuity packets, the information-generating device waits until all of the data has been received and all of the continuity packets have been generated, the network loads required for the transmission may be higher because a larger amount of data is being transmitted at once (e.g., all of the continuity packets are being transmitted in a short time period). The method 400 may proceed to step 412 or step 416.

At step 412, the method 400 may include causing the remote computing device (e.g., the remote computing device 122) to receive the map packet. The map packet may be received from the information-generating device 102. For example, the remote computing device 122 may receive the map packet by way of the remote network adapter 132.

At step 414, the method 400 may include causing the remote computing device to receive continuity packets in an initial order. The continuity packets may be received from the information-generating device 102. For example, continuity packets may be received by the remote computing device 122 by way of the remote network adapter 132 in an initial order where the second continuity packet is received first, the first continuity packet is received second, and the end-of-file continuity packet is received third.

At step 416, the method 400 includes, at the remote computing device, generating an output file. Responsive to receiving at least two of the continuity packets and the map packet, the map packet may be used to generate an output file. The output file may be generated by ordering the continuity packets from the initial order into an output order. For example, given the initial order described above in step 414, the remote processor 124 may order the continuity packets, or contiguous portions of the continuity packets corresponding to contiguous portions of the data, into an output order. The output order may be as follows: 1) the first continuity packet, 2) the second continuity packet, and 3) the end-of-file continuity packet. In some embodiments, as the remote processor receives the continuity packets, the remote processor may contemporaneously generate the output file. For example, the remote computing device 124 may receive the second continuity packet first and the first continuity packet second, but not yet have received the end-of-file continuity packet, after which the remote processor 124 may order the continuity packets into an output order having the first continuity packet first and the second continuity packet second. In some embodiments, while the output file is being generated, the continuity packets are configured to be readable by external processes. Examples of such external processes include maintenance processes configured to check for device maintenance status or error messages. Such external process may be able to read and/or respond to maintenance requests or errors prior to ordering, such that an error message contained in the continuity packets can be read prior to completing the generation of the output file. For example, if a patient is undergoing a CT scan performed by a CT scanner, a processor may monitor and read the data in real-time or near real-time to detect an error message. In this example, if the CT scanner generates a continuity packet containing an error message indicating a fault with the CT scanner (e.g., the data obtained by the CT scanner will be unusable), then, at the direction of such an external monitoring process, the remote processor 124 may read the error message prior to ordering and generating the output file and stop the CT scanner during the CT scan. Stopping the CT scan prior to its completion would limit the patient's unnecessary exposure to X-rays, as any exposure after the error may not result in usable data.

Figure 5A:
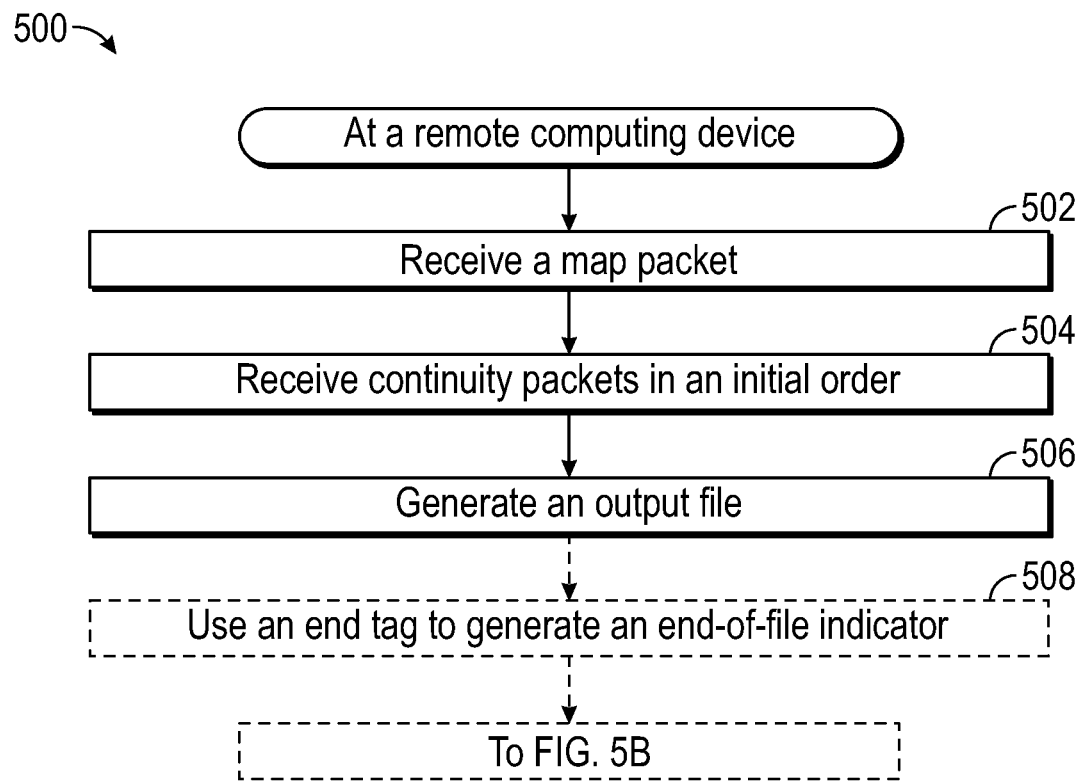
FIGS. 5A and 5B illustrate a method for ordering asynchronous data according to certain aspects of this disclosure.
Figure 5B:
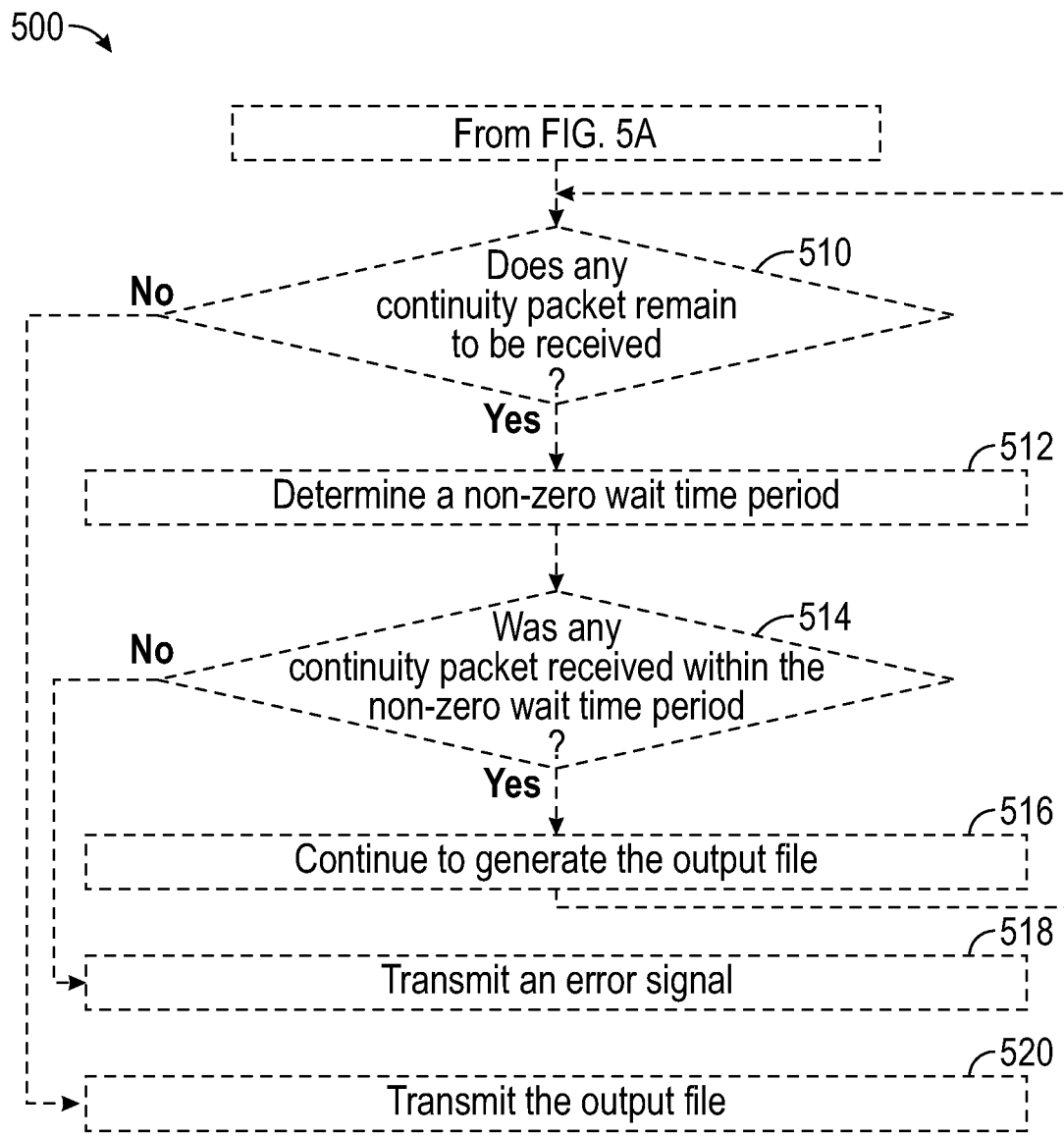

FIGS. 5A and 5B illustrate a computer-implemented method 500 for ordering asynchronous data. The method 500 may be performed by the system 100 using the remote computing device 122. The method 500 may be implemented on a processor, such as the remote processor 124, configured to perform the steps of the method 500. The method 500 may include operations implemented in instructions stored on a memory devices, such as the remote memory 126, and executed on a processor, such as the remote processor 124. The steps of the method 500 may be stored in one or more non-transient computer-readable storage media.

At step 502, the method 500 includes, at the remote computing device (e.g., the remote computing device 122), receiving the map packet. The map packet may be received from the information-generating device 102. For example, the remote computing device 122 may receive the map packet by way of the remote network adapter 132. The map packet contains data mapping information that functions as an indicator of how continuity packets will be received. In some embodiments, the map packet includes end-of-file information that function as information against which data from later-received continuity packets can be compared for determining whether data transmission for a given file has ended. For example, the map packet may contain data mapping information indicating that the continuity packets will have a header following the format of "AA######AA", and an end-of-file continuity packet will have an end-of-file header following the format of "AA######ZZ". In this case, "######" indicates a numerical value starting at "000000" and going to a possible maximum of "999999" and "ZZ" functions as an end tag to indicate that the tagged continuity packet is the final continuity packet of the given file.

At step 504, the method 500 includes, at the remote computing device, receiving continuity packets in an initial order. The continuity packets may be received from the information-generating device 102. For example, continuity packets may be received by the remote computing device 122 by way of the remote network adapter 132 in an initial order where the second continuity packet is received first, the first continuity packet is received second, and the end-of-file continuity packet is received third. Each of the continuity packets is a data packet that includes a contiguous portion of the data. The continuity packets may be generated using the data. For example, the device-side processor 112 may take a contiguous portion of the data and place that contiguous portion into one of the continuity packets. One or more of the continuity packets may include header information that the processor can use to order the continuity packets. For example, a first continuity packet may include a first header including first header information of "AA000000AA", and a second continuity packet may include a second header including second header information of "AA000001AA". A contiguous portion of the data mapping information of the map packet may correspond to a contiguous portion of the header information. For example, the header information may include a contiguous portion of data including the string "AA". The string "AA" corresponds to a portion of the mapping information of the map packet, indicating that header information of relevant continuity packets will contain the string "AA." The header information may also include information pertaining to the portion of data contained in the continuity packet. The information-generating device generates the continuity packets in an initial order; however, a remote computing device 122 may not receive the continuity packets in the initial order (e.g., a first continuity packet may be generated first and a second continuity packet may be generated second, but the second packet may be received before the first packet is received). Thus, the header information may include information that the remote computing device 122 can use to order (e.g., reassemble) the continuity packets, such as in the initial order that the continuity packets were generated. The header information of an end-of-file continuity packet can include an end tag corresponding to a contiguous portion of the end-of-file information. For example, an end-of-file continuity packet may include end-of-file header information of "AA000002ZZ", where "ZZ" functions as the end tag.

At step 506, the method 500 includes, at the remote computing device, generating an output file. Responsive to receiving at least two of the continuity packets and the map packet, the map packet may be used to generate an output file. The output file may be generated by ordering the continuity packets from the initial order into an output order. For example, given the initial order described above in step 504, the remote processor 124 may order the continuity packets, or contiguous portions of the continuity packets corresponding to contiguous portions of the data, into an output order. The output order may be as follows: 1) the first continuity packet, 2) the second continuity packet, and 3) the end-of-file continuity packet. In some embodiments, as the remote processor receives the continuity packets, the remote processor may contemporaneously generate the output file. For example, the remote computing device 124 may receive the second continuity packet first and the first continuity packet second, but not yet have received the end-of-file continuity packet; and after that, the remote processor 124 may order the continuity packets into an output order having the first continuity packet first and the second continuity packet second. In some embodiments, while the output file is being generated, the continuity packets are configured to be readable by external processes. Examples of such external processes include maintenance processes configured to check for device maintenance status or error messages. Such external process may be able to read and/or respond to maintenance requests or errors prior to ordering, such that an error message contained in the continuity packets can be read prior to completing the generation of the output file. For example, if a patient is undergoing a CT scan performed by a CT scanner, a processor may monitor and read the data in real-time or near real-time to detect an error message. In this example, if the CT scanner generates a continuity packet containing an error message indicating a fault with the CT scanner (e.g., the data obtained by the CT scanner will be unusable), then, at the direction of such an external monitoring process, the remote processor 124 may read the error message prior to ordering and generating the output file and stop the CT scanner during the CT scan. Stopping the CT scan prior to its completion would limit the patient's unnecessary exposure to X-rays, as any exposure after the error may not result in usable data.

At step 508, the method 500 may include, at the remote computing device, using the end tag to generate an end-of-file indicator. For example, a flag may be used or a variable may be set as an end-of-file indicator when the end-of-file continuity packet containing the end tag "ZZ" is received (i.e., the remote processor may change a variable "end-of-file-reached" from "false" to "true").

At step 510, the method 500 may include using the header information, the map packet, and the end-of-file indicator to determine whether any continuity packets remain to be received. For example, if the first continuity packet containing the first header information of "AA000000AA" and the end-of-file continuity packet containing the end-of-file header information "AA000002ZZ" (and thus the end tag "ZZ") have been received, the remote processor 124 may determine that the second continuity packet has not been received. If any continuity packets remain to be received, the method 500 proceeds to step 512. If all continuity packets have been received, the method 300 proceeds to step 520.

At step 512, if any continuity packets remain to be received, the method 500 may include determining a non-zero wait time period. For example, if the second continuity packet has not been received, the remote processor 124 may determine a wait time period. The wait time period may be between two seconds and ten seconds, or any other suitable period of time.

At step 514, the method 500 may include, at the remote computing device, determining if any continuity packets were received within the wait time period. For example, if the second continuity packet, which had not been previously received, is received within the wait time period, the remote computing device may determine that a continuity packet was received within the wait time period, subsequent to which the method 500 proceeds to step 516. However, if the second continuity packet is not received within the wait time period, the remote processor 124 may determine that the continuity packet was not received within the wait time period, subsequent to which the method 500 proceeds to step 518.

At step 516, responsive to receiving another continuity packet within the non-zero wait time period, the method 500 may include the remote computing device continuing to generate the output file. For example, if the determination is that the second continuity packet that had not been previously received is received within the wait time period, then the remote processor 124 may continue generating the output file. The method 500 may then return to step 520.

At step 518, responsive to determining the non-zero wait time period and not receiving another continuity packet within the non-zero wait time period, the method 500 may include the remote computing device transmitting an error signal. For example, if the determination is that the second continuity packet that had not been previously received was not received within the wait time period, the remote processor 124 may direct the remote network adapter 132 to transmit an error message and/or the remote output 130 to present the error message (e.g., "Error: Incomplete Data").

At step 520, responsive to determining that every continuity packet has been received, the method 500 includes transmitting the output file. For example, if the first continuity packet, the second continuity packet, and the end-of-file continuity packet have been received and ordered (e.g., into an output file), the remote processor 124 may direct the remote network adapter 132 to transmit the output file via the network 134.

FIGS. 3A, 3B, 4, 5A, and 5B are not intended to be limiting: the methods 300, 400, and 500 can include more or fewer steps and/or processes than those illustrated in FIGS. 3A, 3B, 4, 5A and 5B. Further, the order of the steps of the methods 300, 400, and 500 is not intended to be limiting; the steps can be arranged in any suitable order.

The term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium capable of storing, encoding or carrying a set of instructions for execution by the machine and causing the machine to perform any one or more of the methodologies of the present disclosure. The term "computer-readable storage medium" shall accordingly be taken to include, but not be limited to, solid-state memories, optical media, and magnetic media.

Any of the systems and methods described in this disclosure may be used in connection with rehabilitation. Unless expressly stated otherwise, is to be understood that rehabilitation includes prehabilitation (also referred to as "prehabilitation" or "prehab"). Prehabilitation may be used as a preventative procedure or as a pre-surgical or pre-treatment procedure. Prehabilitation may include any action performed by or on a patient (or directed to be performed by or on a patient, including, without limitation, remotely or distally through telemedicine) to, without limitation, prevent or reduce a likelihood of injury (e.g., prior to the occurrence of the injury); improve recovery time subsequent to surgery; improve strength subsequent to surgery; or any of the foregoing with respect to any non-surgical clinical treatment plan to be undertaken for the purpose of ameliorating or mitigating injury, dysfunction, or other negative consequence of surgical or non-surgical treatment on any external or internal part of a patient's body. For example, a mastectomy may require prehabilitation to strengthen muscles or muscle groups affected directly or indirectly by the mastectomy. As a further non-limiting example, the removal of an intestinal tumor, the repair of a hernia, open-heart surgery or other procedures performed on internal organs or structures, whether to repair those organs or structures, to excise them or parts of them, to treat them, etc., can require cutting through and harming numerous muscles and muscle groups in or about, without limitation, the abdomen, the ribs and/or the thoracic cavity. Prehabilitation can improve a patient's speed of recovery, measure of quality of life, level of pain, etc. in all the foregoing procedures. In one embodiment of prehabilitation, a pre-surgical procedure or a pre-non-surgical-treatment may include one or more sets of exercises for a patient to perform prior to such procedure or treatment. The patient may prepare an area of his or her body for the surgical procedure by performing the one or more sets of exercises, thereby strengthening muscle groups, improving existing and/or establishing new muscle memory, enhancing mobility, improving blood flow, and/or the like.

In some embodiments, the systems and methods described herein may use artificial intelligence and/or machine learning to generate a prehabilitation treatment plan for a user. Additionally, or alternatively, the systems and methods described herein may use artificial intelligence and/or machine learning to recommend an optimal exercise machine configuration for a user. For example, a data model may be trained on historical data such that the data model may be provided with input data relating to the user and may generate output data indicative of a recommended exercise machine configuration for a specific user. Additionally, or alternatively, the systems and methods described herein may use machine learning and/or artificial intelligence to generate other types of recommendations relating to prehabilitation, such as recommended reading material to educate the patient, a recommended health professional specialist to contact, and/or the like.

Consistent with the above disclosure, the examples of systems and method enumerated in the following clauses are specifically contemplated and are intended as a non-limiting set of examples.

Clause 1. A system for transmitting data comprising:
an information-generating device;
a processor in communication with the information-generating device, wherein the processor is configured to:
receive data;
generate a map packet;
transmit the map packet;
using the data, generate continuity packets, wherein each of the continuity packets comprises a contiguous portion of the data;
transmit the continuity packets; and
using the map packet and the continuity packets, cause an output file to be generated.

Clause 2. The system of any clause herein, wherein the processor is further configured to:
cause a remote processor to receive the map packet;
cause the remote processor to receive the continuity packets; and
wherein, responsive to the remote processor receiving the map packet and at least two of the continuity packets, the remote processor generates the output file.

Clause 3. The system of any clause herein, wherein, as the continuity packets are received, the remote processor generates the output file in real-time or near real time.

Clause 4. The system of any clause herein, wherein the remote processor receives the continuity packets in an initial order; and
wherein, using the map packet, the processor is configured to cause the remote processor to generate the output file by ordering the continuity packets from the initial order into an output order.

Clause 5. The system of any clause herein, wherein one or more of the continuity packets comprise header information; and
wherein a contiguous portion of the map packet corresponds to a contiguous portion of the header information.

Clause 6. The system of any clause herein, wherein each of the continuity packets comprises header information.

Clause 7. The system of any clause herein, wherein the map packet comprises end-of-file information;
wherein one or more of the continuity packets comprise header information; and
wherein header information of an end-of-file continuity packet comprises an end tag corresponding to a contiguous portion of the end-of-file information.

Clause 8. The system of any clause herein, wherein the information-generating device comprises a medical device.

Clause 9. The system of any clause herein, wherein the medical device is an orthopedic rehabilitation device.

Clause 10. The system of any clause herein, further comprising a memory device operatively coupled to the processor, wherein the memory device stores instructions, and wherein the processor is configured to execute the instructions.

Clause 11. A method for operating an information-generating device, comprising:
receiving data;
generating a map packet;
transmitting the map packet;

using the data to generate continuity packets, wherein each of the continuity packets comprises a contiguous portion of the data;

transmitting the continuity packets; and using the map packet and the continuity packets to cause an output file to be generated.

Clause 12. The method of any clause herein, further comprising:

causing a remote processor to receive the map packet;

causing the remote processor to receive the continuity packets; and wherein, responsive to the remote processor receiving the map packet and at least two of the continuity packets, the remote processor generates the output file.

Clause 13. The method of any clause herein, wherein, as the continuity packets are received, the remote processor generates the output file in real-time or near real time.

Clause 14. The method of any clause herein, wherein the remote processor receives the continuity packets in an initial order; and wherein, using the map packet, the method further comprises causing the remote processor to generate the output file by ordering the continuity packets from the initial order into an output order.

Clause 15. The method of any clause herein, wherein one or more of the continuity packets comprise header information; and wherein a contiguous portion of the map packet corresponds to a contiguous portion of the header information.

Clause 16. The method of any clause herein, wherein each of the continuity packets comprises header information.

Clause 17. The method of any clause herein, wherein the map packet comprises end-of-file information;

wherein one or more of the continuity packets comprise header information; and wherein header information of an end-of-file continuity packet comprises an end tag corresponding to a contiguous portion of the end-of-file information.

Clause 18. The method of any clause herein, wherein the information-generating device comprises a medical device.

Clause 19. The method of any clause herein, wherein the medical device is an orthopedic rehabilitation device.

Clause 20. A tangible, non-transitory computer-readable storage medium storing instructions that, when executed, cause a processor to:

receive data from an information-generating device;

generate a map packet;

transmit the map packet;

using the data, generate continuity packets, wherein each of the continuity packets comprises a contiguous portion of the data;

transmit the continuity packets; and using the map packet and the continuity packets, cause an output file to be generated.

Clause 21. The tangible, non-transitory computer-readable storage medium of any clause herein, wherein the instructions further cause the processor to:

cause a remote processor to receive the map packet;

cause the remote processor to receive the continuity packets; and responsive to the remote processor receiving the map packet and at least two of the continuity packets, cause the remote processor to generate the output file.

Clause 22. The tangible, non-transitory computer-readable storage medium of any clause herein, wherein, as the continuity packets are received, the remote processor generates the output file.

Clause 23. The tangible, non-transitory computer-readable storage medium of any clause herein, wherein the remote processor receives the continuity packets in an initial order; and wherein, using the map packet, the instructions further cause the processor to cause the remote processor to generate the output file by ordering the continuity packets from the initial order into an output order.

Clause 24. The tangible, non-transitory computer-readable storage medium of any clause herein, wherein one or more of the continuity packets comprise header information; and wherein a contiguous portion of the map packet corresponds to a contiguous portion of the header information.

Clause 25. The tangible, non-transitory computer-readable storage medium of any clause herein, wherein each of the continuity packets comprises header information.

Clause 26. The tangible, non-transitory computer-readable storage medium of any clause herein wherein the map packet comprises end-of-file information;

wherein one or more of the continuity packets comprise header information; and wherein header information of an end-of-file continuity packet comprises an end tag corresponding to a contiguous portion of the end-of-file information.

Clause 27. The tangible, non-transitory computer-readable storage medium of any clause herein, wherein the information-generating device comprises a medical device.

Clause 28. The tangible, non-transitory computer-readable storage medium of any preceding clause, wherein the medical device is an orthopedic rehabilitation device.

Clause 29. A system for ordering of asynchronously transmitted data, comprising:

a processor configured to:

receive, from an information-generating device, a map packet;

receive, from the information-generating device, continuity packets in an initial order; and responsive to receiving the map packet and at least two of the continuity packets, use the map packet to generate an output file by ordering the continuity packets from the initial order into an output order.

Clause 30. The system of any clause herein, wherein, as the continuity packets are received, the processor is configured to generate the output file in real-time or near real time.

Clause 31. The system of any clause herein, wherein, while the output file is being generated, the continuity packets are configured to be readable by external processes.

Clause 32. The system of any clause herein, wherein one or more of the continuity packets comprise header information; and wherein a contiguous portion of the map packet corresponds to a contiguous portion of the header information.

Clause 33. The system of any clause herein, wherein each of the continuity packets comprises header information.

Clause 34. The system of any clause herein, wherein the map packet comprises end-of-file information;

wherein one or more of the continuity packets comprise header information; and wherein header information of an end-of-file continuity packet comprises an end tag corresponding to a contiguous portion of the end-of-file information.

Clause 35. The system of any clause herein, wherein, using the end tag, the processor is further configured to generate an end-of-file indication.

Clause 36. The system of any clause herein, wherein the processor is further configured to:
use the header information, the map packet, and the end-of-file indication, to determine whether any continuity packet remains to be received;
responsive to any continuity packets remaining to be received, determine a non-zero wait time period;
responsive to receiving another continuity packet within the non-zero wait time period, continue to generate the output file; and
responsive to receiving no further continuity packets within the non-zero wait time period, transmit an error signal.

Clause 37. The system of any clause herein, wherein the processor is further configured to:
use the header information, the map packet, and the end-of-file indication to determine whether every continuity packet has been received; and
if every continuity packet has been received, transmit the output file.

Clause 38. The system of any clause herein, wherein the information-generating device comprises a medical device.

Clause 39. The system of any clause herein, wherein the medical device is an orthopedic rehabilitation device.

Clause 40. The system of any clause herein, further comprising a memory device operatively coupled to the processor, wherein the memory device stores instructions, and wherein the processor is configured to execute the instructions.

Clause 41. A method for operating a computing device, comprising:
receiving, from an information-generating device, a map packet;
receiving, from the information-generating device, continuity packets in an initial order; and
responsive to receiving the map packet and at least two of the continuity packets, using the map packet to generate an output file by ordering the continuity packets from the initial order into an output order.

Clause 42. The method of any clause herein, wherein, as the continuity packets are received, the output file is generated in real-time or near real-time.

Clause 43. The method of any clause herein, wherein, while the output file is being generated, the continuity packets are configured to be readable by external processes.

Clause 44. The method of any clause herein, wherein one or more of the continuity packets comprise header information; and
wherein a contiguous portion of the map packet corresponds to a contiguous portion of the header information.

Clause 45. The method of any clause herein, wherein each of the continuity packets comprises header information.

Clause 46. The method of any clause herein, wherein the map packet comprises end-of-file information;
wherein one or more of the continuity packets comprise header information; and
wherein header information of an end-of-file continuity packet comprises an end tag corresponding to a contiguous portion of the end-of-file information.

Clause 47. The method of any clause herein, further comprising using the end tag to generate an end-of-file indication.

Clause 48. The method of any clause herein, further comprising:
using the header information, the map packet, and the end-of-file indication to determine whether every continuity packet has been received;
responsive to any continuity packets remaining to be received, determining a non-zero wait time period;
responsive to receiving another continuity packet within the non-zero wait time period, continuing to generate the output file; and
responsive to receiving no further continuity packets within the non-zero wait time period, transmitting an error signal.

Clause 49. The method of any clause herein, further comprising:
using the header information, the map packet, and the end-of-file indication to determine whether every continuity packet has been received; and
if every continuity packet has been received, transmitting the output file.

Clause 50. The method of any clause herein, wherein the information-generating device comprises a medical device.

Clause 51. The method of any clause herein, wherein the medical device is an orthopedic rehabilitation device.

Clause 52. A tangible, non-transitory computer-readable storage medium storing instructions that, when executed, cause a processor to:
receive, from an information-generating device, a map packet;
receive, from the information-generating device, continuity packets in an initial order; and
responsive to receiving the map packet and at least two of the continuity packets, using the map packet to generate an output file by ordering the continuity packets from the initial order into an output order.

Clause 53. The tangible, non-transitory computer-readable storage medium of any clause herein, wherein, as the continuity packets are received, the processor contemporaneously generates the output file.

Clause 54. The tangible, non-transitory computer-readable storage medium of any clause herein, wherein the continuity packets are configured to be readable by external processes while the output file is being generated.

Clause 55. The tangible, non-transitory computer-readable storage medium of any clause herein, wherein one or more of the continuity packets comprise header information; and
wherein a contiguous portion of the map packet corresponds to a contiguous portion of the header information.

Clause 56. The tangible, non-transitory computer-readable storage medium of any clause herein, wherein each of the continuity packets comprises header information.

Clause 57. The tangible, non-transitory computer-readable storage medium of any clause herein, wherein the map packet comprises end-of-file information;
wherein one or more of the continuity packets comprise header information; and
wherein header information of an end-of-file continuity packet comprises an end tag corresponding to a contiguous portion of the end-of-file information.

Clause 58. The tangible, non-transitory computer-readable storage medium of any preceding clause, wherein the instructions further cause the processor to use the end tag to generate an end-of-file indication.

Clause 59. The tangible, non-transitory computer-readable storage medium of any clause herein, wherein the instructions further cause the processor to:
  use the header information, the map packet, and the end-of-file indication, to determine whether any continuity packet remains to be received;
  responsive to any continuity packet remaining to be received, determine a non-zero wait time period;
  responsive to receiving another continuity packet within the non-zero wait time period, continue generating the output file; and
  responsive to receiving no further continuity packets within the non-zero wait time period, transmit an error signal.

Clause 60. The tangible, non-transitory computer-readable storage medium of any clause herein, wherein the instructions further cause the processor to:
  use the header information, the map packet, and the end-of-file indication to determine whether every continuity packet has been received; and
  responsive to determining that every continuity packet has been received, transmit the output file.

Clause 61. The tangible, non-transitory computer-readable storage medium of any clause herein, wherein the information-generating device comprises a medical device.

Clause 62. The tangible, non-transitory computer-readable storage medium of any preceding clause, wherein the medical device is an orthopedic rehabilitation device.

Clause 63. A system for transmitting data and ordering asynchronous data, comprising:
  an information-generating device comprising a device-side processor configured to:
    receive data;
    generate a map packet;
    transmit the map packet;
    use the data to generate continuity packets, wherein each of the continuity packets comprises a contiguous portion of the data;
    transmit the continuity packets; and
  a remote computing device comprising a remote processor configured to:
    receive, from the information-generating device, the map packet;
    receive, from the information-generating device, the continuity packets in an initial order; and
    responsive to receiving at least two of the continuity packets and the map packet, use the map packet to generate an output file by ordering the continuity packets from the initial order into an output order.

Clause 64. The system of any clause herein, wherein, as the remote processor receives the continuity packets, the remote processor contemporaneously generates the output file.

Clause 65. The system of any clause herein, wherein, while the output file is being generated, the continuity packets are configured to be readable by external processes.

Clause 66. The system of any clause herein, wherein one or more of the continuity packets comprise header information; and
  wherein a contiguous portion of the map packet corresponds to a contiguous portion of the header information.

Clause 67. The system of any clause herein, wherein each of the continuity packets comprises header information.

Clause 68. The system of any clause herein, wherein the map packet comprises end-of-file information;
  wherein one or more of the continuity packets comprise header information; and
  wherein header information of an end-of-file continuity packet comprises an end tag corresponding to a contiguous portion of the end-of-file information.

Clause 69. The system of any clause herein, wherein the remote processor is further configured to, using the end tag, generate an end-of-file indication.

Clause 70. The system of any clause herein, wherein the remote processor is further configured to:
  use the header information, the map packet, and the end-of-file indication to determine whether any continuity packets remain to be received;
  if any continuity packets remain to be received, determine a non-zero wait time period;
  responsive to determining the non-zero wait time period and receiving another continuity packet within the non-zero wait time period, continue generating the output file; and
  responsive to determining the non-zero wait time period and not receiving another continuity packet within the non-zero wait time period, transmit an error signal.

Clause 71. The system of any clause herein, wherein the remote processor is further configured to:
  use the header information, the map packet, and the end-of-file indication to determine whether every continuity packet has been received; and
  responsive to determining that every continuity packet has been received, transmit the output file.

Clause 72. The system of any clause herein, wherein the information-generating device comprises a medical device.

Clause 73. The system of any clause herein, wherein the medical device is an orthopedic rehabilitation device.

Clause 74. The system of any clause herein, further comprising a device-side memory device operatively coupled to the device-side processor, wherein the device-side memory device stores device-side instructions, and wherein the device-side processor is configured to execute the device-side instructions.

Clause 75. The system of any clause herein, further comprising a remote memory device operatively coupled to the remote processor, wherein the remote memory device stores remote instructions, and wherein the remote processor is configured to execute the remote instructions.

Clause 76. A computer-implemented system, comprising:
  an electromechanical device configured to be manipulated by a patient while performing an exercise session;
  a processor in communication with the electromechanical device, wherein the processor is configured to:
  receive data;
  generate a map packet;
  transmit the map packet;
  using the data, generate continuity packets, wherein each of the continuity packets comprises a contiguous portion of the data;
  transmit the continuity packets; and
  using the map packet and the continuity packets, cause an output file to be generated.

Clause 77. The computer-implemented system of any clause herein, wherein the processor is further configured to:
  cause a remote processor to receive the map packet;
  cause the remote processor to receive the continuity packets; and wherein, responsive to the remote processor receiving the map packet and at least two of the continuity packets, the remote processor generates the output file.

Clause 78. The computer-implemented system of any clause herein, wherein, as the continuity packets are received, the remote processor generates the output file in real-time or near real time.

No part of the description in this application should be read as implying that any particular element, step, or function is an essential element that must be included in the claim scope. The scope of patented subject matter is defined only by the claims. Moreover, none of the claims is intended to invoke 35 U.S.C. § 112(f) unless the exact words "means for" are followed by a participle.

The foregoing description, for purposes of explanation, use specific nomenclature to provide a thorough understanding of the described embodiments. However, it should be apparent to one skilled in the art that the specific details are not required to practice the described embodiments. Thus, the foregoing descriptions of specific embodiments are presented for purposes of illustration and description. They are not intended to be exhaustive or to limit the described embodiments to the precise forms disclosed. It should be apparent to one of ordinary skill in the art that many modifications and variations are possible in view of the above teachings.

The above discussion is meant to be illustrative of the principles and various embodiments of the present invention. Once the above disclosure is fully appreciated, numerous variations and modifications will become apparent to those skilled in the art. It is intended that the following claims be interpreted to embrace all such variations and modifications.

What is claimed is:

1. A method for operating a remote processor, comprising:
   receiving a map packet;
   receiving at least two continuity packets, wherein each comprises a contiguous portion of data, wherein:
      another processor generates the map packet and uses data received by an electromechanical device to generate the at least two continuity packets, and
      the remote processor receives the at least two continuity packets in an initial order; and
   generating, using the map packet, an output file in real-time or near real-time, wherein:
      the remote processor generates the output file by ordering the at least two continuity packets from the initial order into an output order, wherein the output order is one of the same order as the initial order or a reordering of the initial order.

2. The method of claim 1, wherein one or more of the at least two continuity packets comprise header information.

3. The method of claim 2, wherein a contiguous portion of the map packet corresponds to a contiguous portion of the header information.

4. The method of claim 1, wherein each of the at least two continuity packets comprises header information.

5. The method of claim 1, wherein the map packet comprises end-of-file information.

6. The method of claim 1, wherein header information of an end-of-file continuity packet comprises an end tag corresponding to a contiguous portion of end-of-file information in the map packet.

7. The method of claim 1, wherein the electromechanical device comprises a rehabilitation device.

8. A system comprising:
   a memory device storing instructions; and
   a remote processor communicatively coupled to the memory device, wherein the remote processor executes the instructions to:
   receive a map packet;
   receive at least two continuity packets, wherein each comprises a contiguous portion of data, wherein:
      another processor generates the map packet and uses data received by an electromechanical device to generate the at least two continuity packets, and
      the remote processor receives the at least two continuity packets in an initial order; and
   generate, using the map packet, an output file in real-time or near real-time, wherein:
      the remote processor generates the output file by ordering the at least two continuity packets from the initial order into an output order, wherein the output order is one of the same order as the initial order or a reordering of the initial order.

9. The system of claim 8, wherein one or more of the at least two continuity packets comprise header information.

10. The system of claim 9, wherein a contiguous portion of the map packet corresponds to a contiguous portion of the header information.

11. The system of claim 8, wherein each of the at least two continuity packets comprises header information.

12. The system of claim 9, wherein the map packet comprises end-of-file information.

13. The system of claim 8, wherein header information of an end-of-file continuity packet comprises an end tag corresponding to a contiguous portion of end-of-file information in the map packet.

14. The system of claim 8, wherein the electromechanical device comprises a rehabilitation device.

15. A tangible, non-transitory computer-readable medium storing instructions that, when executed, cause a remote processor to:
   receive a map packet;
   receive at least two continuity packets, wherein each comprises a contiguous portion of data, wherein:
      another processor generates the map packet and uses data received by an electromechanical device to generate the at least two continuity packets, and
      the remote processor receives the at least two continuity packets in an initial order; and
   generate, using the map packet, an output file in real-time or near real-time, wherein:
      the remote processor generates the output file by ordering the at least two continuity packets from the initial order into an output order, wherein the output order is one of the same order as the initial order or a reordering of the initial order.

16. The computer-readable medium of claim 15, wherein one or more of the at least two continuity packets comprise header information.

17. The computer-readable medium of claim 16, wherein a contiguous portion of the map packet corresponds to a contiguous portion of the header information.

18. The computer-readable medium of claim 15, wherein each of the at least two continuity packets comprises header information.

* * * * *